US009965076B2

(12) United States Patent
McMillen

(10) Patent No.: US 9,965,076 B2
(45) Date of Patent: May 8, 2018

(54) PIEZORESISTIVE SENSORS AND APPLICATIONS

(71) Applicant: Kesumo LLC, Berkeley, CA (US)

(72) Inventor: Keith A. McMillen, Berkeley, CA (US)

(73) Assignee: BeBop Sensors, Inc., Berkeley, CA (US)

( * ) Notice: Subject to any disclaimer, the term of this patent is extended or adjusted under 35 U.S.C. 154(b) by 41 days.

(21) Appl. No.: 14/299,976

(22) Filed: Jun. 9, 2014

(65) Prior Publication Data

US 2015/0331522 A1 Nov. 19, 2015

Related U.S. Application Data

(60) Provisional application No. 61/993,953, filed on May 15, 2014.

(51) Int. Cl.
G06F 1/16 (2006.01)
G06F 3/045 (2006.01)
G01L 1/18 (2006.01)
A61B 5/00 (2006.01)
G01L 9/00 (2006.01)
(Continued)

(52) U.S. Cl.
CPC .......... G06F 3/0414 (2013.01); A61B 5/6804 (2013.01); A61B 5/6843 (2013.01); G01L 1/18 (2013.01); G01L 5/228 (2013.01); G01L 9/0052 (2013.01); G01R 27/00 (2013.01); G06F 1/16 (2013.01); G06F 1/163 (2013.01); G06F 3/012 (2013.01); G06F 3/045 (2013.01); G06F 3/0416 (2013.01); A61B 2562/0247 (2013.01); A61B 2562/046 (2013.01); G06F 2203/04102 (2013.01)

(58) Field of Classification Search
CPC ......... G01L 1/18; G01L 9/0052; G01L 5/228; G01L 5/0019; G06F 3/0414; G06F 3/045; G06F 2203/04103; A61B 2562/0247; A61B 2562/046; A61B 5/6843; A61B 5/6804; A61B 5/6806; A61B 5/6807; A61B 2090/064
See application file for complete search history.

(56) References Cited

U.S. PATENT DOCUMENTS 4,294,014 A 10/1981 Baumann et al.
4,438,291 A 3/1984 Eichelberger et al.
(Continued)

FOREIGN PATENT DOCUMENTS

CN 200980381 Y 11/2007
CN 201920728 U 8/2011
(Continued)

OTHER PUBLICATIONS

U.S. Notice of Allowance dated May 1, 2015 issued in U.S. Appl. No. 14/173,617.
(Continued)

Primary Examiner — Dismery Mercedes
(74) Attorney, Agent, or Firm — Weaver Austin Villeneuve & Sampson LLP

(57) ABSTRACT

Sensors incorporating piezoresistive materials are described. One class of sensors includes piezoresistive material that is held or otherwise supported adjacent conductive traces on a substrate. Another class of sensors includes conductive traces formed directly on the piezoresistive material.

35 Claims, 14 Drawing Sheets

(51) Int. Cl.
*G06F 3/041* (2006.01)
*G06F 3/01* (2006.01)
*G01L 5/22* (2006.01)
*G01R 27/00* (2006.01)

(56) References Cited

U.S. PATENT DOCUMENTS

| | | | |
|---|---|---|---|
| 4,489,302 A | 12/1984 | Eventoff | |
| 4,693,530 A | 9/1987 | Stillie et al. | |
| 4,745,301 A | 5/1988 | Michalchik | |
| 4,790,968 A * | 12/1988 | Ohkawa | H01C 10/106 |
| | | | 200/264 |
| 4,852,443 A | 8/1989 | Duncan et al. | |
| 5,033,291 A | 7/1991 | Podoloff et al. | |
| 5,128,880 A | 7/1992 | White | |
| 5,131,306 A | 7/1992 | Yamamoto | |
| 5,219,292 A | 6/1993 | Dickirson et al. | |
| 5,237,520 A | 8/1993 | White | |
| 5,288,938 A | 2/1994 | Wheaton | |
| 5,316,017 A | 5/1994 | Edwards et al. | |
| 5,429,092 A | 7/1995 | Kamei | |
| 5,571,973 A * | 11/1996 | Taylot | A61B 5/1036 |
| | | | 73/862.046 |
| 5,578,766 A | 11/1996 | Kondo | |
| 5,624,132 A | 4/1997 | Blackburn et al. | |
| 5,659,395 A | 8/1997 | Brown et al. | |
| 5,695,859 A | 12/1997 | Burgess | |
| 5,729,905 A | 3/1998 | Mathiasmeier et al. | |
| 5,822,223 A | 10/1998 | Genest | |
| 5,866,829 A | 2/1999 | Pecoraro | |
| 5,878,359 A | 3/1999 | Takeda | |
| 5,943,044 A | 8/1999 | Martinelli et al. | |
| 5,989,700 A | 11/1999 | Krivopal | |
| 6,029,358 A | 2/2000 | Mathiasmeier et al. | |
| 6,032,109 A | 2/2000 | Ritmiller, III | |
| 6,049,327 A | 4/2000 | Walker et al. | |
| 6,087,930 A | 7/2000 | Kulka et al. | |
| 6,121,869 A | 9/2000 | Burgess | |
| 6,141,643 A | 10/2000 | Harmon | |
| 6,155,120 A * | 12/2000 | Taylor | A61B 5/1036 |
| | | | 73/862.046 |
| 6,215,055 B1 | 4/2001 | Saravis | |
| 6,216,545 B1 | 4/2001 | Taylor | |
| 6,304,840 B1 | 10/2001 | Vance et al. | |
| 6,331,893 B1 | 12/2001 | Brown et al. | |
| 6,360,615 B1 | 3/2002 | Smela | |
| 6,486,776 B1 | 11/2002 | Pollack et al. | |
| 6,763,320 B2 | 7/2004 | Kimble | |
| 6,815,602 B2 | 11/2004 | De Franco | |
| 6,822,635 B2 | 11/2004 | Shahoian et al. | |
| 6,829,942 B2 | 12/2004 | Yanai et al. | |
| 6,964,205 B2 * | 11/2005 | Papakostas | G01L 1/20 |
| | | | 73/862.046 |
| 7,037,268 B1 * | 5/2006 | Sleva | B06B 1/0688 |
| | | | 340/855.6 |
| 7,066,887 B2 | 6/2006 | Flesch et al. | |
| 7,109,068 B2 | 9/2006 | Akram et al. | |
| 7,113,856 B2 | 9/2006 | Theiss et al. | |
| 7,157,640 B2 | 1/2007 | Baggs | |
| 7,302,866 B1 | 12/2007 | Malkin et al. | |
| 7,311,009 B2 | 12/2007 | Kotovsky | |
| 7,332,670 B2 | 2/2008 | Fujiwara et al. | |
| 7,409,256 B2 | 8/2008 | Lin et al. | |
| 7,439,465 B2 | 10/2008 | Parkinson | |
| 7,493,230 B2 | 2/2009 | Schwartz et al. | |
| 7,536,794 B2 | 5/2009 | Hay et al. | |
| 7,608,776 B2 | 10/2009 | Ludwig | |
| 7,719,007 B2 | 5/2010 | Tompkins et al. | |
| 7,754,956 B2 | 7/2010 | Gain et al. | |
| 7,780,541 B2 | 8/2010 | Bauer | |
| 7,855,718 B2 | 12/2010 | Westerman | |
| 7,928,312 B2 | 4/2011 | Sharma | |
| 7,984,544 B2 | 6/2011 | Rosenberg | |
| 8,109,149 B2 * | 2/2012 | Kotovsky | G01L 1/18 |
| | | | 438/51 |
| 8,117,922 B2 | 2/2012 | Xia et al. | |
| 8,120,232 B2 * | 2/2012 | Daniel | G01L 1/16 |
| | | | 310/330 |
| 8,127,623 B2 * | 3/2012 | Son | G01L 1/146 |
| | | | 178/18.06 |
| 8,161,826 B1 | 4/2012 | Taylor | |
| 8,274,485 B2 | 9/2012 | Liu et al. | |
| 8,346,684 B2 | 1/2013 | Mirbach et al. | |
| 8,368,505 B2 * | 2/2013 | Deppiesse | H03K 17/965 |
| | | | 338/114 |
| 8,448,530 B2 | 5/2013 | Leuenberger et al. | |
| 8,479,585 B2 | 7/2013 | Shaw-Klein | |
| 8,536,880 B2 | 9/2013 | Philipp | |
| 8,571,827 B2 | 10/2013 | Jang et al. | |
| 8,680,390 B2 | 3/2014 | McMillen et al. | |
| 8,813,579 B2 | 8/2014 | Aufrere | |
| 8,857,274 B2 * | 10/2014 | Mamigonians | G01L 1/142 |
| | | | 73/862.626 |
| 8,884,913 B2 | 11/2014 | Saynac et al. | |
| 8,892,051 B2 * | 11/2014 | Yi | H04W 68/00 |
| | | | 340/425.5 |
| 8,904,876 B2 | 12/2014 | Taylor et al. | |
| 8,925,392 B2 * | 1/2015 | Esposito | A61B 5/1036 |
| | | | 73/862.01 |
| 8,925,393 B2 * | 1/2015 | Cannard | D04B 1/14 |
| | | | 73/862 |
| 8,945,328 B2 | 2/2015 | Longinotti-Buitoni et al. | |
| 8,947,889 B2 | 2/2015 | Kelley et al. | |
| 8,964,205 B2 * | 2/2015 | Shimizu | G06K 15/1817 |
| | | | 358/1.1 |
| 8,970,513 B2 | 3/2015 | Kwon et al. | |
| 9,032,804 B2 * | 5/2015 | Granado | G01L 9/0052 |
| | | | 73/700 |
| 9,038,482 B2 | 5/2015 | Xia et al. | |
| 9,075,404 B2 | 7/2015 | McMillen et al. | |
| 9,076,419 B2 * | 7/2015 | McMillen | G10H 1/02 |
| 9,112,058 B2 | 8/2015 | Bao et al. | |
| 9,164,586 B2 | 10/2015 | Zellers et al. | |
| 9,271,665 B2 * | 3/2016 | Sarrafzadeh | G01L 1/18 |
| 9,417,693 B2 | 8/2016 | Seth | |
| 9,442,614 B2 | 9/2016 | McMillen | |
| 9,480,582 B2 | 11/2016 | Lundborg | |
| 9,529,433 B2 | 12/2016 | Shankar et al. | |
| 9,546,921 B2 | 1/2017 | McMillen et al. | |
| 9,652,101 B2 | 5/2017 | McMillen et al. | |
| 9,696,833 B2 | 7/2017 | McMillen | |
| 9,710,060 B2 | 7/2017 | McMillen et al. | |
| 9,721,553 B2 | 8/2017 | McMillen et al. | |
| 9,753,568 B2 | 9/2017 | McMillen | |
| 9,827,996 B2 | 11/2017 | McMillen | |
| 9,836,151 B2 | 12/2017 | McMillen | |
| 2002/0078757 A1 | 6/2002 | Hines et al. | |
| 2004/0031180 A1 * | 2/2004 | Ivanov | F41A 17/20 |
| | | | 42/70.11 |
| 2004/0093746 A1 | 5/2004 | Varsallona | |
| 2004/0183648 A1 * | 9/2004 | Weber | G01L 5/0052 |
| | | | 338/47 |
| 2004/0189145 A1 | 9/2004 | Pletner et al. | |
| 2005/0109095 A1 | 5/2005 | Sinnett | |
| 2007/0129776 A1 | 6/2007 | Robins et al. | |
| 2007/0151348 A1 * | 7/2007 | Zdeblick | G01L 9/045 |
| | | | 73/708 |
| 2007/0188179 A1 * | 8/2007 | Deangelis | G01D 5/2405 |
| | | | 324/661 |
| 2007/0188180 A1 | 8/2007 | Deangelis et al. | |
| 2007/0202765 A1 * | 8/2007 | Krans | G06F 3/0414 |
| | | | 442/301 |
| 2007/0234888 A1 | 10/2007 | Rotolo De Moraes | |
| 2008/0069412 A1 | 3/2008 | Champagne et al. | |
| 2008/0158145 A1 | 7/2008 | Westerman | |
| 2008/0189827 A1 | 8/2008 | Bauer | |
| 2008/0254824 A1 | 10/2008 | Rotolo de Moraes | |
| 2009/0049980 A1 | 2/2009 | Sharma | |
| 2009/0237374 A1 * | 9/2009 | Li | G06F 3/0414 |
| | | | 345/174 |
| 2009/0272197 A1 * | 11/2009 | Ridao Granado | G01L 1/20 |
| | | | 73/828 |
| 2009/0301190 A1 | 12/2009 | Ross, Jr. et al. | |

(56) References Cited

U.S. PATENT DOCUMENTS

| | | | |
|---|---|---|---|
| 2009/0303400 A1* | 12/2009 | Hou | G06F 3/0412 349/12 |
| 2010/0066572 A1* | 3/2010 | Dietz | H01H 13/702 341/34 |
| 2010/0123686 A1* | 5/2010 | Klinghult | G06F 3/0412 345/178 |
| 2010/0134327 A1 | 6/2010 | Dinh et al. | |
| 2010/0149108 A1 | 6/2010 | Hotelling et al. | |
| 2010/0179724 A1 | 7/2010 | Weston | |
| 2010/0199777 A1 | 8/2010 | Hooper et al. | |
| 2010/0242274 A1* | 9/2010 | Rosenfeld | G06F 3/03543 29/848 |
| 2010/0274447 A1* | 10/2010 | Stumpf | G01D 1/00 701/36 |
| 2010/0286951 A1 | 11/2010 | Danenberg et al. | |
| 2010/0292945 A1 | 11/2010 | Reynolds et al. | |
| 2010/0315337 A1 | 12/2010 | Ferren et al. | |
| 2011/0088535 A1 | 4/2011 | Zarimis | |
| 2011/0088536 A1* | 4/2011 | McMillen | G10H 1/348 84/746 |
| 2011/0107771 A1 | 5/2011 | Crist et al. | |
| 2011/0141052 A1 | 6/2011 | Bernstein et al. | |
| 2011/0153261 A1 | 6/2011 | Jang et al. | |
| 2011/0221564 A1 | 9/2011 | Deppiesse et al. | |
| 2011/0241850 A1 | 10/2011 | Bosch et al. | |
| 2011/0246028 A1 | 10/2011 | Lisseman et al. | |
| 2011/0260994 A1* | 10/2011 | Saynac | G06F 3/0414 345/173 |
| 2011/0271772 A1 | 11/2011 | Parks et al. | |
| 2011/0279409 A1* | 11/2011 | Salaverry | G06F 3/0416 345/174 |
| 2012/0007831 A1 | 1/2012 | Chang et al. | |
| 2012/0024132 A1 | 2/2012 | Wallace et al. | |
| 2012/0026124 A1 | 2/2012 | Li et al. | |
| 2012/0055257 A1* | 3/2012 | Shaw-Klein | H01L 41/081 73/780 |
| 2012/0143092 A1 | 6/2012 | Xia et al. | |
| 2012/0191554 A1 | 7/2012 | Xia et al. | |
| 2012/0197161 A1 | 8/2012 | Xia et al. | |
| 2012/0198949 A1 | 8/2012 | Xia et al. | |
| 2012/0222498 A1 | 9/2012 | Mamigonians | |
| 2012/0234105 A1 | 9/2012 | Taylor | |
| 2012/0283979 A1 | 11/2012 | Bruekers et al. | |
| 2012/0296528 A1 | 11/2012 | Wellhoefer et al. | |
| 2012/0297885 A1 | 11/2012 | Hou et al. | |
| 2012/0299127 A1 | 11/2012 | Fujii et al. | |
| 2012/0312102 A1 | 12/2012 | Alvarez et al. | |
| 2012/0323501 A1* | 12/2012 | Sarrafzadeh | G01L 1/18 702/41 |
| 2013/0009905 A1 | 1/2013 | Castillo et al. | |
| 2013/0055482 A1 | 3/2013 | D'Aprile et al. | |
| 2013/0082970 A1* | 4/2013 | Frey | G06F 3/0414 345/173 |
| 2013/0085394 A1 | 4/2013 | Corbett, III et al. | |
| 2013/0113057 A1* | 5/2013 | Taylor | G01L 1/18 257/417 |
| 2013/0165809 A1 | 6/2013 | Abir | |
| 2013/0192071 A1 | 8/2013 | Esposito et al. | |
| 2013/0203201 A1* | 8/2013 | Britton | G01K 7/226 438/54 |
| 2013/0211208 A1* | 8/2013 | Varadan | A61B 5/14552 600/301 |
| 2013/0239787 A1 | 9/2013 | McMillen et al. | |
| 2013/0274985 A1 | 10/2013 | Lee et al. | |
| 2013/0275057 A1 | 10/2013 | Perlin et al. | |
| 2013/0327560 A1 | 12/2013 | Ichiki | |
| 2013/0340598 A1 | 12/2013 | Marquez et al. | |
| 2014/0007704 A1* | 1/2014 | Granado | G01L 9/0052 73/862.627 |
| 2014/0013865 A1* | 1/2014 | White | G01L 1/14 73/862.626 |
| 2014/0026678 A1* | 1/2014 | Cannard | D04B 1/14 73/862.041 |
| 2014/0033829 A1 | 2/2014 | Xia et al. | |
| 2014/0090488 A1 | 4/2014 | Taylor et al. | |
| 2014/0104776 A1 | 4/2014 | Clayton et al. | |
| 2014/0107966 A1 | 4/2014 | Xia et al. | |
| 2014/0107967 A1 | 4/2014 | Xia et al. | |
| 2014/0107968 A1 | 4/2014 | Xia et al. | |
| 2014/0125124 A1 | 5/2014 | Verner | |
| 2014/0130593 A1* | 5/2014 | Ciou | A61B 5/1038 73/172 |
| 2014/0150573 A1* | 6/2014 | Cannard | G01L 1/18 73/862.627 |
| 2014/0182170 A1 | 7/2014 | Wawrousek et al. | |
| 2014/0195023 A1 | 7/2014 | Statham et al. | |
| 2014/0215684 A1 | 8/2014 | Hardy et al. | |
| 2014/0222243 A1 | 8/2014 | McMillen et al. | |
| 2014/0318699 A1* | 10/2014 | Longinotti-Buitoni | A61B 5/0002 156/247 |
| 2014/0347076 A1 | 11/2014 | Barton et al. | |
| 2015/0035743 A1 | 2/2015 | Rosener | |
| 2015/0084873 A1 | 3/2015 | Hagenbuch et al. | |
| 2015/0086955 A1 | 3/2015 | Poniatowski et al. | |
| 2015/0130698 A1 | 5/2015 | Burgess | |
| 2015/0168238 A1* | 6/2015 | Raut | G01N 27/048 702/42 |
| 2015/0177080 A1 | 6/2015 | Esposito et al. | |
| 2015/0261372 A1 | 9/2015 | McMillen et al. | |
| 2015/0316434 A1 | 11/2015 | McMillen et al. | |
| 2015/0317964 A1 | 11/2015 | McMillen et al. | |
| 2015/0330855 A1 | 11/2015 | Daniecki et al. | |
| 2015/0331512 A1 | 11/2015 | McMillen et al. | |
| 2015/0331523 A1 | 11/2015 | McMillen et al. | |
| 2015/0331524 A1 | 11/2015 | McMillen et al. | |
| 2015/0331533 A1 | 11/2015 | McMillen et al. | |
| 2015/0370396 A1 | 12/2015 | Hotelling et al. | |
| 2016/0054798 A1 | 2/2016 | Messinger et al. | |
| 2016/0070347 A1 | 3/2016 | McMillen et al. | |
| 2016/0147352 A1 | 5/2016 | Filiz et al. | |
| 2016/0169754 A1 | 6/2016 | Kowalewski et al. | |
| 2016/0175186 A1 | 6/2016 | Shadduck | |
| 2016/0238547 A1* | 8/2016 | Park | C08K 7/00 |
| 2016/0252412 A1 | 9/2016 | McMillen et al. | |
| 2016/0270727 A1 | 9/2016 | Berg et al. | |
| 2016/0278709 A1* | 9/2016 | Ridao Granado | A61B 5/0205 |
| 2016/0318356 A1 | 11/2016 | McMillen et al. | |
| 2016/0375910 A1 | 12/2016 | McMillen et al. | |
| 2017/0038881 A1 | 2/2017 | McMillen | |
| 2017/0110103 A1 | 4/2017 | McMillen et al. | |
| 2017/0167931 A1 | 6/2017 | McMillen et al. | |
| 2017/0212638 A1 | 7/2017 | McMillen | |
| 2017/0303853 A1 | 10/2017 | McMillen et al. | |
| 2017/0305301 A1 | 10/2017 | McMillen et al. | |

FOREIGN PATENT DOCUMENTS

| | | |
|---|---|---|
| CN | 102551728 A | 7/2012 |
| CN | 202396601 U | 8/2012 |
| CN | 203234132 U | 10/2013 |
| CN | 102406280 B | 3/2014 |
| DE | 102 12 023 A1 | 10/2003 |
| DE | 11 2010 004 038 T5 | 9/2012 |
| EP | 0 014 022 B1 | 11/1984 |
| EP | 2 682 724 A1 | 1/2014 |
| JP | H08-194481 | 7/1996 |
| JP | 2000-267664 A | 9/2000 |
| JP | 2008-515008 A | 5/2008 |
| KR | 2007/0008500 A | 1/2007 |
| KR | 100865148 B1 | 10/2008 |
| KR | 10-1362742 B1 | 2/2014 |
| KR | 2014/0071693 A | 6/2014 |
| NL | 8900820 A | 11/1990 |
| RU | 2 533 539 C1 | 11/2014 |
| WO | WO 99/020179 A1 | 4/1999 |
| WO | WO 2007/024875 A2 | 3/2007 |
| WO | WO 2009/155891 A1 | 12/2009 |
| WO | WO 2011/047171 | 4/2011 |
| WO | WO 2015/175317 A1 | 11/2015 |
| WO | PCT/US16/19513 | 2/2016 |
| WO | PCT/US16/29528 | 4/2016 |

(56) References Cited

FOREIGN PATENT DOCUMENTS

| WO | WO 2016/070078 A1 | 5/2016 |
| WO | WO 2016/138234 A1 | 9/2016 |
| WO | PCT/US16/55997 | 10/2016 |
| WO | WO 2016/176307 A1 | 11/2016 |
| WO | WO 2016/210173 A1 | 12/2016 |
| WO | WO 2017/066096 A1 | 4/2017 |
| WO | WO 2017/184367 A1 | 10/2017 |

OTHER PUBLICATIONS

U.S. Office Action dated Apr. 2, 2015 issued in U.S. Appl. No. 13/799,304.
U.S. Notice of Allowance dated Apr. 24, 2015 issued in U.S. Appl. No. 13/799,304.
U.S. Office Action dated Sep. 1, 2015 issued in U.S. Appl. No. 14/728,872.
PCT International Search Report and Written Opinion dated Sep. 3, 2015 issued in PCT/US2015/029732.
"Electronic Foot Size Measuring Devices," *Sensatech Research Ltd., Custom Electronic Sensing Solutions,* Registered Office: 4 Heath Square, Boltro Road, Haywards Heath, RH16 1BL Company Registration No. 4524018 Cardiff [retrieved at http:www.electronicsarena.co.uk/companies/sensatech-researcb/products/electronic-foot-size-measureing-devices on Sep. 17, 2015], 3 pages.
"iStep® Digital Foot Scan," (© 2002-2015) [retrieved at http://www.foot.com/site/iStep on Sep. 17, 2015], 1 page.
"Podotech Elftman," and Podotech Elftman Brochure (UK Version) [retrieved at http://www.podotech.com/diagnostics/podotech-elftman-2/ on Sep. 17, 2015] podo+tech®, Foot Care Technology Solutions, 7 pages.
"The Emed®-Systems," [retrieved at http://www.novel.de/novelcontent/emed on Sep. 17, 2015] novel.de, 4 pages.
U.S. Appl. No. 14/464,551, filed Aug. 20, 2014, McMillen.
U.S. Office Action dated Sep. 12, 2012 issued in U.S. Appl. No. 12/904,657.
U.S. Office Action dated Apr. 15, 2013 issued in U.S. Appl. No. 12/904,657.
U.S. Notice of Allowance dated Nov. 8, 2013 issued in U.S. Appl. No. 12/904,657.
U.S. Office Action dated Mar. 12, 2015 issued in U.S. Appl. No. 14/173,617.
PCT International Search Report dated May 27, 2011, issued in PCT/US2010/052701.
PCT International Preliminary Report on Patentability and Written Opinion dated Apr. 26, 2012, issued in PCT/US2010/052701.
Japanese Office Action dated Feb. 25, 2014 issued in JP 2012-534361.
Roh, Jung-Sim et al. (2011) "Robust and reliable fabric and piezoresistive multitouch sensing surfaces for musical controllers," from Alexander Refsum Jensenius, Recorded at: *11th International Conference on New Interfaces for Musical Expression* May 30-Jun. 1, 2011, Oslo, Norway, a vimeo download at http://vimeo.com/26906580.
U.S. Appl. No. 15/052,293, filed Feb. 24, 2016, McMillen et al.
U.S. Office Action dated Mar. 10, 2016 issued in U.S. Appl. No. 14/727,619.
U.S. Final Office Action dated Mar. 9, 2016 issued in U.S. Appl. No. 14/728,872.
U.S. Office Action dated Jan. 13, 2016 issued in U.S. Appl. No. 14/464,551.
U.S. Appl. No. 15/138,802, filed Apr. 26, 2016, McMillen.
U.S. Final Office Action dated Jul. 18, 2016 issued in U.S. Appl. No. 14/727,619.
U.S. Office Action dated Jun. 22, 2016 issued in U.S. Appl. No. 14/728,872.
U.S. Office Action dated Jul. 25, 2016 issued in U.S. Appl. No. 14/728,873.
U.S. Notice of Allowance dated Jun. 23, 2016 issued in U.S. Appl. No. 14/464,551.
U.S. Office Action dated Jun. 28, 2016 issued in U.S. Appl. No. 14/671,844.
U.S. Office Action dated May 20, 2016 issued in U.S. Appl. No. 14/928,058.
PCT International Search Report and Written Opinion dated May 26, 2016 issued in PCT/US2016/019513.
PCT International Search Report and Written Opinion dated Apr. 14, 2016 issued in PCT/US2015/058370.
U.S. Notice of Allowance dated Sep. 15, 2016 issued in U.S. Appl. No. 14/727,619.
U.S. Appl. No. 15/251,772, filed Aug. 30, 2016, McMillen.
U.S. Appl. No. 15/287,520, filed Oct. 6, 2016, McMillen et al.
U.S. Appl. No. 15/374,816, filed Dec. 9, 2016, McMillen et al.
U.S. Final Office Action dated Oct. 18, 2016 issued in U.S. Appl. No. 14/728,872.
U.S. Office Action dated Dec. 30, 2016 issued in U.S. Appl. No. 14/728,873.
U.S. Office Action dated Sep. 23, 2016 issued in U.S. Appl. No. 14/800,538.
U.S. Notice of Allowance dated Jan. 17, 2017 issued in U.S. Appl. No. 14/800,538.
U.S. Final Office Action dated Nov. 25, 2016 issued in U.S. Appl. No. 14/671,844.
U.S. Final Office Action dated Jan. 6, 2017 issued in U.S. Appl. No. 14/928,058.
U.S. Office Action dated Dec. 27, 2016 issued in U.S. Appl. No. 15/287,520.
PCT International Preliminary Report on Patentability and Written Opinion dated Nov. 24, 2016 issued in PCT/US2015/029732.
PCT International Search Report and Written Opinion dated Sep. 15, 2016 issued in PCT/US2016/029528.
PCT International Search Report and Written Opinion dated Sep. 29, 2016 issued in PCT/US2016/039089.
U.S. Advisory Action dated Feb. 10, 2017 issued in U.S. Appl. No. 14/728,872.
U.S. Final Office Action dated Mar. 31, 2017 issued in U.S. Appl. No. 14/728,873.
U.S. Office Action dated Feb. 22, 2017 issued in U.S. Appl. No. 14/671,821.
U.S. Notice of Allowance dated Mar. 13, 2017 issued in U.S. Appl. No. 14/671,844.
U.S. Office Action dated Jan. 26, 2017 issued in U.S. Appl. No. 15/052,293.
U.S. Final Office Action dated May 2, 2017 issued in U.S. Appl. No. 15/052,293.
U.S. Notice of Allowance dated Mar. 16, 2017 issued in U.S. Appl. No. 14/928,058.
U.S. Notice of Allowance dated Mar. 27, 2017 issued in U.S. Appl. No. 15/287,520.
PCT International Preliminary Report on Patentability and Written Opinion dated May 11, 2017 issued in PCT/US2015/058370.
PCT International Search Report and Written Opinion dated Jan. 19, 2017 issued in PCT/US2016/055997.
U.S. Appl. No. 15/479,103, filed Apr. 4, 2017, McMillen et al.
U.S. Appl. No. 15/483,926, filed Apr. 10, 2017, McMillen.
U.S. Office Action dated May 19, 2017 issued in U.S. Appl. No. 14/728,872.
U.S. Advisory Action and Examiner initiated interview summary dated May 26, 2017 issued in U.S. Appl. No. 14/728,873.
U.S. Notice of Allowance dated Jul. 3, 2017 issued in U.S. Appl. No. 14/671,821.
U.S. Office Action dated Jun. 30, 2017 issued in U.S. Appl. No. 15/251,772.
U.S. Notice of Allowance dated May 24, 2017 issued in U.S. Appl. No. 15/052,293.
U.S. Notice of Allowance [Supplemental Notice of Allowability] dated Jun. 20, 2017 issued in U.S. Appl. No. 15/052,293.
U.S. Office Action dated Jun. 23, 2017 issued in U.S. Appl. No. 15/190,089.
U.S. Appl. No. 15/621,935, filed Jun. 13, 2017, McMillen et al.
U.S. Appl. No. 15/630,840, filed Jun. 22, 2017, McMillen et al.
U.S. Notice of Allowance dated Oct. 16, 2017 issued in U.S. Appl. No. 14/728,872.

(56) References Cited

OTHER PUBLICATIONS

U.S. Office Action dated Aug. 25, 2017 issued in U.S. Appl. No. 14/728,873.
U.S. Final Office Action dated Nov. 15, 2017 issued in U.S. Appl. No. 15/251,772.
U.S. Notice of Allowance dated Sep. 22, 2017 issued in U.S. Appl. No. 15/052,293.
U.S. Notice of Allowance [Supplemental Notice of Allowability] dated Oct. 19, 2017 issued in U.S. Appl. No. 15/052,293.
U.S. Office Action dated Nov. 3, 2017 issued in U.S. Appl. No. 15/138,802.
U.S. Notice of Allowance dated Aug. 10, 2017 issued in U.S. Appl. No. 15/190,089.
PCT International Preliminary Report on Patentability and Written Opinion dated Sep. 8, 2017 issued in PCT/US2016/019513.
PCT International Preliminary Report on Patentability and Written Opinion dated Oct. 31, 2017 issued in PCT/US2016/029528.
PCT International Search Report and Written Opinion dated Aug. 14, 2017 issued in PCT/US2017/026812.
U.S. Appl. No. 15/690,108, filed Aug. 29, 2017, McMillen et al.
U.S. Appl. No. 15/835,131, filed Dec. 7, 2017, McMillen et al.

\* cited by examiner

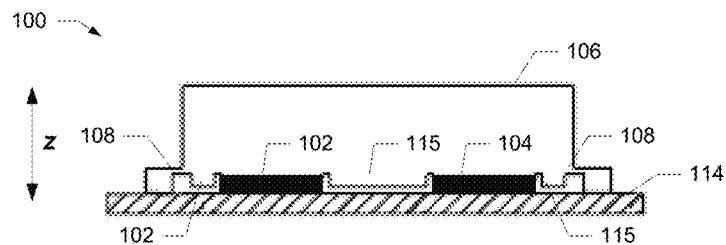
FIG. 1A
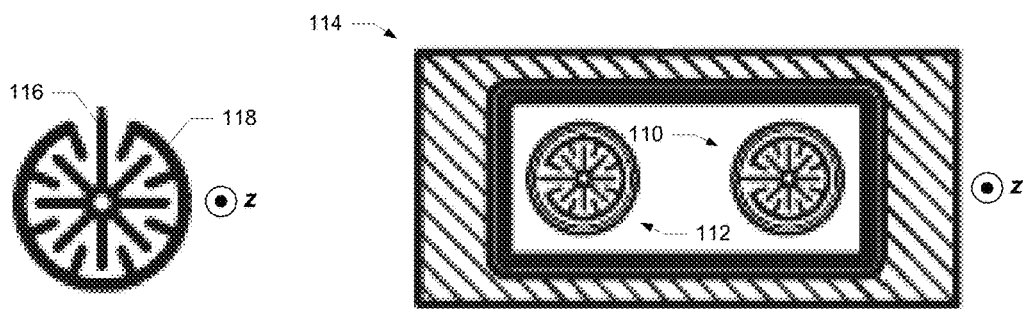
FIG. 1B  FIG. 1C
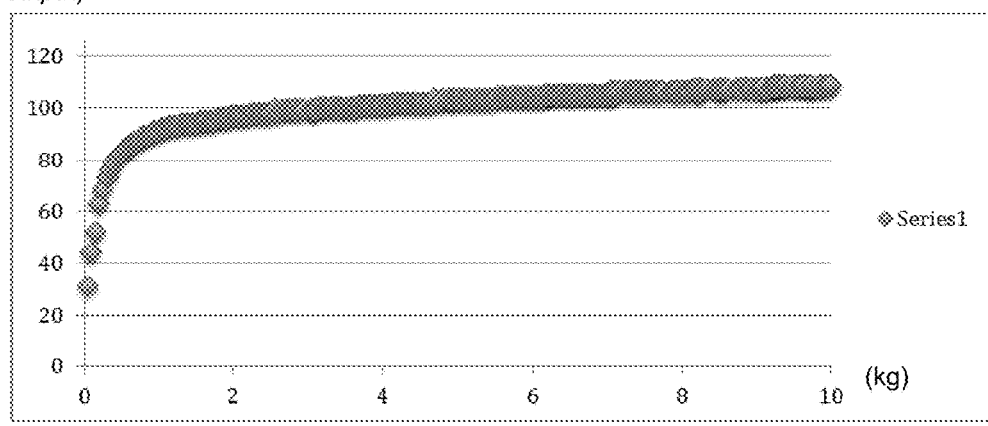
FIG. 1D

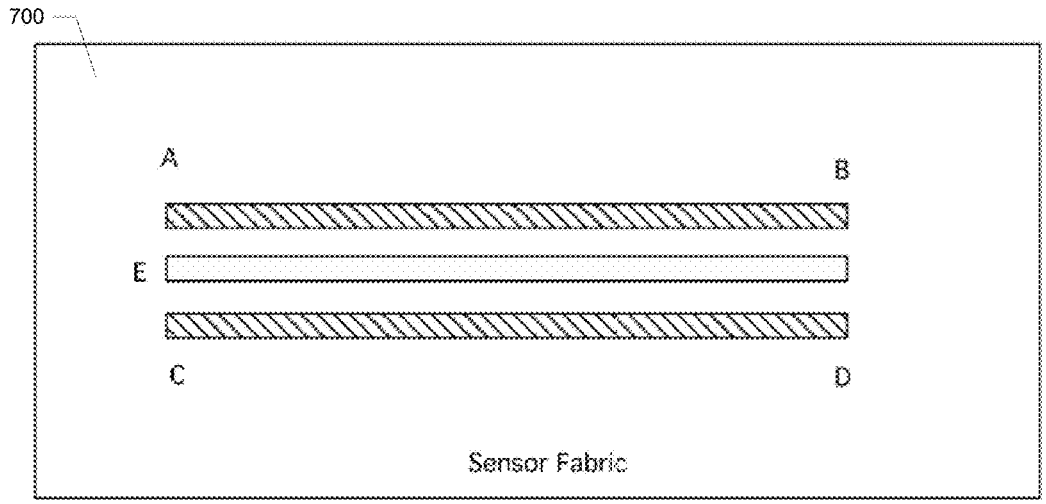

Unique electrical signal sent into points A, B, C, D succesively or sumultaneously. Conductors AB and CD are approx 10% of relaxed surface resistance of Sensor fabric.

Conductor E has near zero resistance and measures each of the signals based on increasing pressure to sensor material between elements which reduces resistance causing larger signals of A, B, C, D to be seen on E.

Using ratios of A - B and total Amplitude of A+B position and pressure can be determined.

Measuring ratios of above between signals A-B and C-D location of pressure can be determined between.

If wide contact point or multiple contact points appear along the conductors, a conductive plane behind sensor fabric will allow measurement of signals passed through the fabric to remove ambiguity.

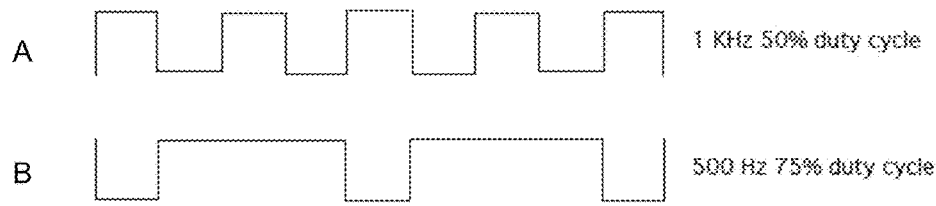

*FIG. 7*

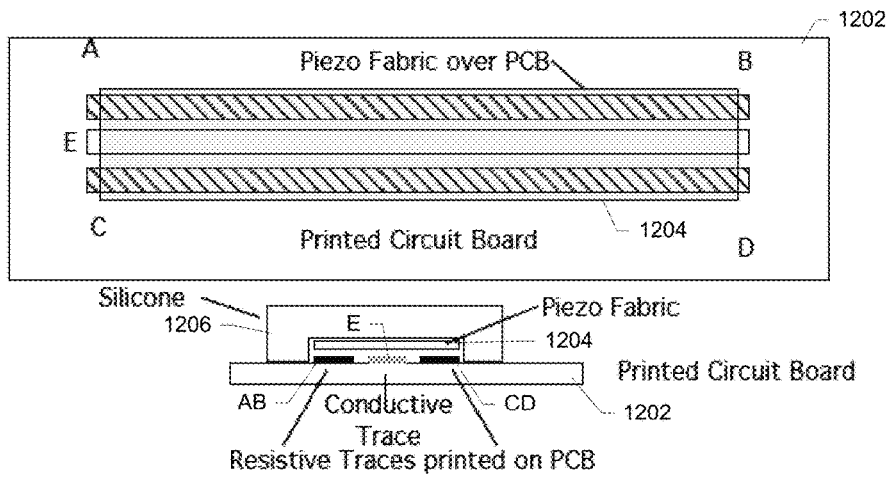

A variation where the conductive trace (normal copper ) of a PCB has two parallel printed ink resistors alongside. The piezo fabric is held over the three traces in a silicone geometry that compresses when pressed shorting the three traces.

Unique electrical signal sent into points A, B, C, D succesively or sumultaneously. Conductors AB and CD are approx 10% of relaxed surface resistance of Sensor fabric.

Conductor E has near zero resistance andmeasures each
of the signals based on increasing pressure to
sensor material between elements which reduces resistance causing larger signals of A, B, C, D to be seen on E.

Using ratios of A - B and total Amplitude of A+B position and pressure
can be determined.

Measuring ratios of above between signals A-B and C-D location of pressure can be determined between.

If wide contact point or multiple contact points appear along the conductors,
a conductive plane behind sensor fabric will allow measurement of signals passed through the fabric to remove ambiguity.

*FIG. 12*

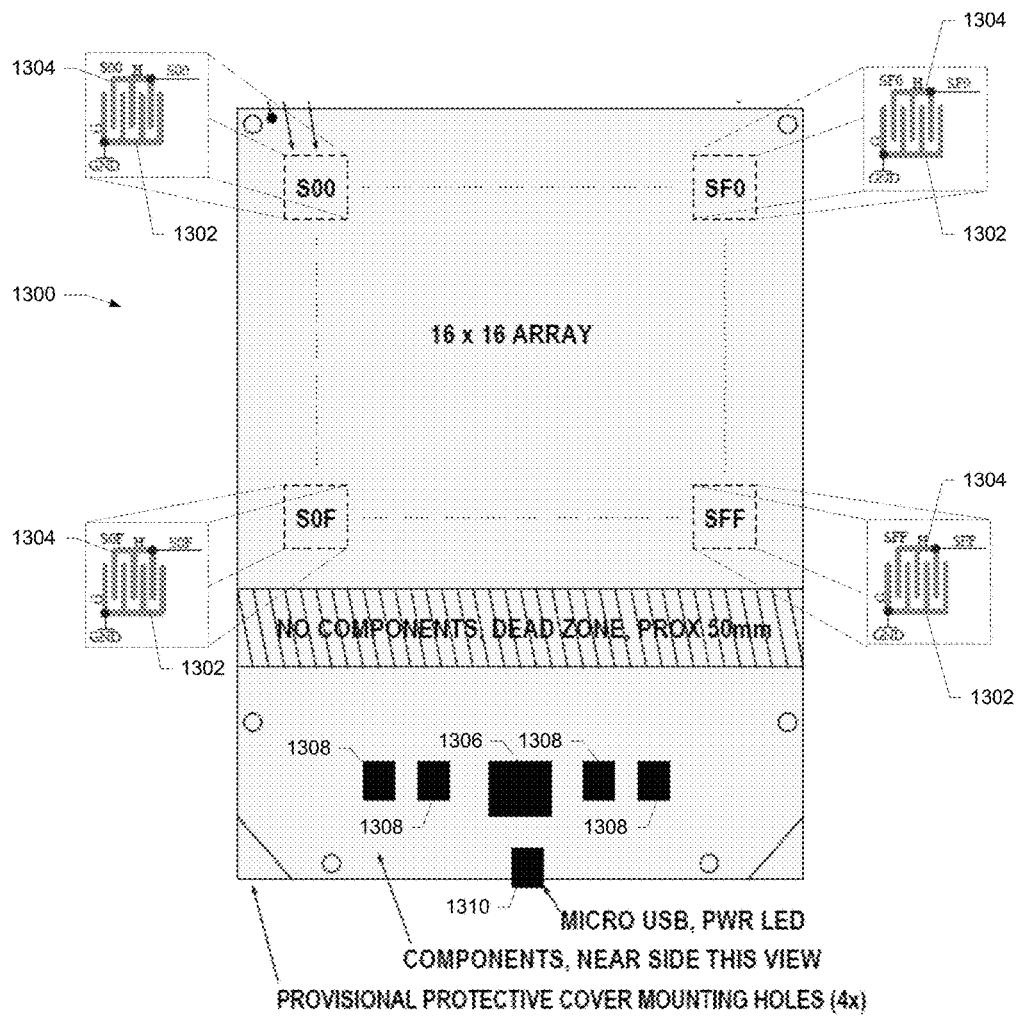
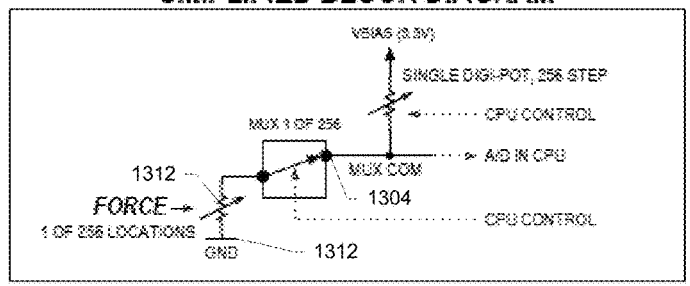
FIG. 13

PIEZORESISTIVE SENSORS AND APPLICATIONS

RELATED APPLICATION DATA

The present application is a nonprovisional application and claims priority under 35 U.S.C. 119(e) to U.S. Provisional Patent Application No. 61/993,953 entitled Piezoresistive Sensors and Applications filed on May 15, 2014, the entire disclosure of which is incorporated herein by reference for all purposes.

BACKGROUND

Demand is rapidly rising for technologies that bridge the gap between the computing devices and the physical world. These interfaces typically require some form of sensor technology that translates information from the physical domain to the digital domain. The "Internet of Things" contemplates the use of sensors in a virtually limitless range of applications, for many of which conventional sensor technology is not well suited.

SUMMARY

According to various implementations, sensors and applications of sensors are provided. According to a particular class of implementations, a sensor includes a flexible piezoresistive substrate and two or more conductive traces formed directly on the piezoresistive substrate.

According to some implementations, the sensor includes circuitry configured to receive one or more signals from the conductive traces, and to detect a touch event with reference to the one or more signals. According to some of these implementations, the circuitry is further configured to determine either or both of a location of the touch event, and a magnitude of force of the touch event.

According to some implementations, the piezoresistive substrate is a piezoresistive fabric. According to others, the piezoresistive substrate is a piezoresistive rubber.

According to some implementations, the conductive traces comprise a conductive ink printed on the piezoresistive substrate. According to others, the conductive traces comprise conductive paint deposited on the piezoresistive substrate.

According to some implementations, the conductive traces are formed only on one side of the piezoresistive substrate. According to others, the conductive traces are formed on two opposing sides of the piezoresistive substrate.

According to some implementations, an insulating material formed over a first one of the conductive traces, wherein at least a portion of a second one of the conductive traces is formed over the insulating material and the first conductive trace.

According to some implementations, the two or more conductive traces include a first conductive trace characterized by a first conductivity and a second conductive trace characterized by a second conductivity lower than the first conductivity. The sensor further includes circuitry configured to drive one end of the second conductive trace with a first signal characterized by a first duty cycle, and to drive an opposing end of the second conductive trace with a second signal characterized by a second duty cycle. The circuitry is further configured to receive a mixed signal from the first conductive trace; the mixed signal including contributions from the first and second signals via the piezoresistive substrate. The circuitry is further configured to detect a location of a touch event along a first axis of the second conductive trace with reference to the contributions of the first and second signals to the mixed signal.

According to some implementations, the conductive traces are arranged in a first parallel array of the conductive traces oriented in a first direction formed on one side of the piezoresistive substrate, and second parallel array of the conductive traces oriented at 90 degrees to the first array formed an opposing side of the piezoresistive substrate. The sensor includes circuitry configured to sequentially drive the first array of conductive traces, and to sequentially scan the second array of conductive traces. The circuitry is further configured to determine a location and a magnitude of force for each of one or more touch events with reference to signals received from the second array of conductive traces.

According to some implementations, the conductive traces are arranged in quadrants, and the sensor includes circuitry configured to detect a touch event with reference to signals received from the conductive traces of the quadrants. The circuitry is further configured to determine a location of the touch event, a magnitude of force of the touch event, a speed of motion of the touch event, and a direction of motion of the touch event.

According to some implementations, the conductive traces are arranged in a plurality of conductive trace groups. Each of the conductive trace groups includes two or more of the conductive traces. The resistance between the conductive traces in each of the conductive trace groups varies with force applied to the piezoresistive substrate in a vicinity of the conductive trace group. The sensor includes circuitry configured to receive one or more signals from each of the conductive trace groups and generate control information in response thereto. The control information being for controlling operation of one or more processes or devices in communication with the circuitry.

According to some implementations, the piezoresistive substrate is one or more pieces of piezoresistive fabric integrated with a cap for wearing on a human head. Each of the pieces of piezoresistive fabric has an array of the conductive traces thereon. The sensor includes circuitry configured to detect a touch event with reference to signals received from the conductive traces. The circuitry is further configured to determine a location of the touch event and a magnitude of force of the touch event.

A further understanding of the nature and advantages of various implementations may be realized by reference to the remaining portions of the specification and the drawings.

BRIEF DESCRIPTION OF THE DRAWINGS

FIGS. 1A-1D illustrate a particular sensor configuration.
FIG. 7 illustrates another sensor configuration and a technique for acquiring sensor data.
FIG. 12 illustrates another sensor configuration and a technique for acquiring sensor data.

FIG. 13 illustrates a test system for piezoresistive materials.

DETAILED DESCRIPTION

Figure 2A:
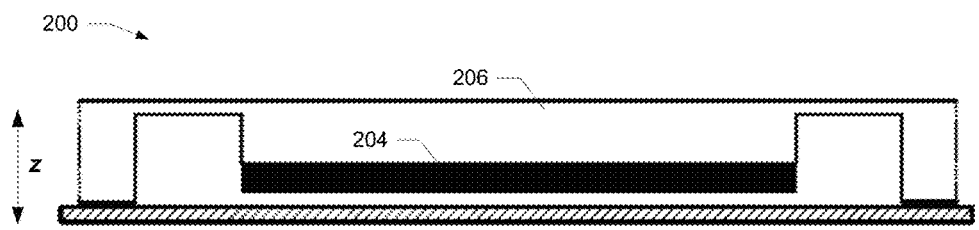
FIGS. 2A-2D illustrate another sensor configuration.

Sensors incorporating piezoresistive materials are described in this disclosure. Specific implementations are described below including the best modes contemplated. Examples of these implementations are illustrated in the accompanying drawings. However, the scope of this disclosure is not limited to the described implementations. Rather, this disclosure is intended to cover alternatives, modifications, and equivalents of these implementations. In the following description, specific details are set forth in order to provide a thorough understanding of the described implementations. Some implementations may be practiced without some or all of these specific details. In addition, well known features may not have been described in detail to promote clarity.

Piezoresistive materials include any of a class of materials that exhibits a change in electrical resistance in response to mechanical force or pressure applied to the material. One class of sensors includes piezoresistive material that is held or otherwise supported (e.g., within a silicone key or control pad) in proximity to conductive traces arranged on a substrate (e.g., a printed circuit board (PCB)). Another class of sensors includes conductive traces formed directly on a flexible substrate of piezoresistive material, e.g., a piezoresistive fabric or other flexible material. When force or pressure is applied to either type of sensor, the resistance between traces connected by the piezoresistive material changes in a time-varying manner that is representative of the applied force. A signal representative of the magnitude of the applied force is generated based on the change in resistance. This signal is captured via the conductive traces (e.g., as a voltage or a current), digitized (e.g., via an analog-to-digital converter), processed (e.g., by an associated processor or controller or suitable control circuitry), and mapped (e.g., by the associated processor, controller, or control circuitry) to a control function that may be used in conjunction with virtually any type of process, device, or system. In some implementations, arrays of conductive traces having various configurations are used to determine the direction and/or velocity of the applied force in one or more dimensions (e.g., in addition to the magnitude of the force or pressure).

A particular class of implementations builds on designs described in U.S. patent application Ser. No. 12/904,657 entitled Foot-Operated Controller, now U.S. Pat. No. 8,680,390, and U.S. patent application Ser. No. 13/799,304 entitled Multi-Touch Pad Controller, published as U.S. Patent Publication No. 2013/0239787, the entire disclosures of which are incorporated herein by reference for all purposes. In some of these implementations the piezoresistive material is held just off the conductive traces in a flexible key or control pad structure constructed of, for example, silicone. By controlling the geometry of the silicone, the pattern and density of the conductive traces, and the distance of the piezoresistive material from the trace pattern, a variety of sensors can be constructed that have very different response curves and dynamic ranges that are appropriate for a wide range of different applications. It should be noted that the following sensor designs may employ any of the configurations and techniques described in the attached disclosures in various combinations.

FIGS. 1A-1C illustrate a particular sensor configuration 100 useful for implementing the keys of an electronic keyboard. The depicted sensor configuration is intended to be sensitive to a light touch, but also have a dynamic range that is sufficient to provide a significant range of expressiveness for its musician users. Two piezoresistive components 102 and 104 allow the musician to rock key 106 forward and backward to achieve a variety of desired effects, e.g., note bending, vibrato, etc.

A cantilever structure 108 in silicone key 106 (a webbing element that connects the key to a surrounding framing structure and suspends the key within the structure) allows it to collapse evenly and easily, bringing piezoresistive elements 102 and 104 into contact with the corresponding conductive trace patterns 110 and 112 on PCB 114 with very little pressure, e.g., 30-50 grams. The silicone includes stops 115 that resist the vertical travel of the key and define the placement of piezoresistive components 102 and 104. Stops 115 are configured to reduce the effect of higher magnitude forces on the sensor output. The conductive trace patterns by which the change in resistance is measured are configured as a star or asterisk 116 within a spoked circle 118. The density of the trace pattern, the proximity of the piezoresistive components to the conductive traces, and the configuration of the silicone results in a response curve (FIG. 1D) in which only 30-40 grams of pressure results in a significant drop in resistance. The x-axis of the curve represents kilograms of force and the y-axis represents a linearly scaled representation of the sensor's 7-bit analog-to-digital converter output. The curve flattens out after about 8-10 kg, but provides sufficient dynamic range to allow a significant degree of expressiveness.

Figure 2B:
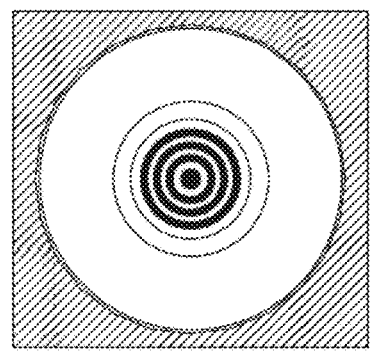
Figure 2C:
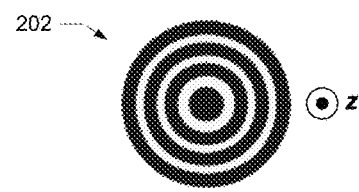
Figure 2D:
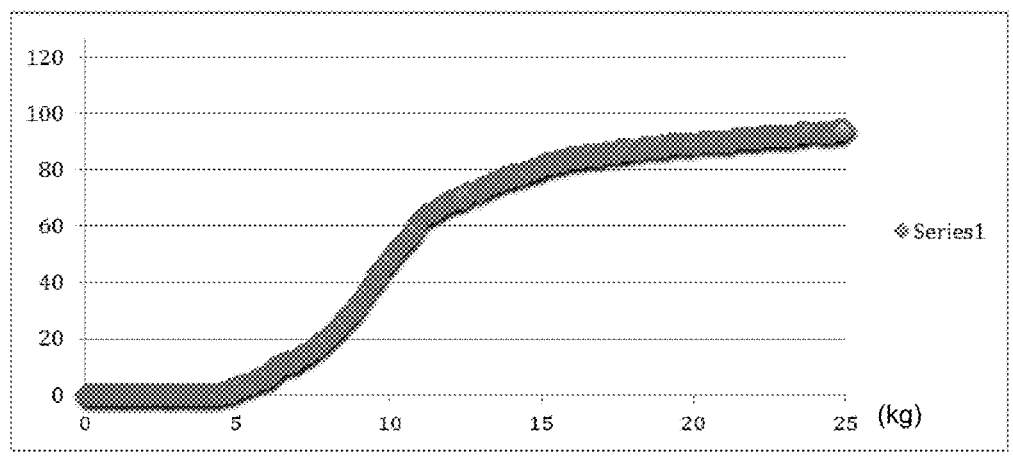

FIGS. 2A-2C illustrate another sensor configuration 200 intended to handle a higher range of force than the sensor configuration of FIGS. 1A-1C. The conductive traces are arranged in a concentric pattern of rings 202 with the change in resistance being measured between adjacent rings. Given its trace pattern density, the spacing of piezoresistive material 204 from the conductive traces, and the overall mechanical resistance of structure 206 to force, this sensor configuration doesn't register much of a response until about 5 kg of force is applied (FIG. 2D). On the other hand, this configuration has useful dynamic range out past 25 kg. Again, the x-axis of the curve represents kilograms of force and the y-axis represents a linearly scaled representation of the sensor's 7-bit analog-to-digital converter output.

Even with careful attention paid to the various elements of the sensor configuration, the dynamic range of a sensor configuration is ultimately limited by the dynamic range of the piezoresistive material itself. According to a particular class of implementations, the range of the piezoresistive material employed is about 40 dB (i.e., about 100:1). This may not be sufficient for some applications. Therefore, according to a particular class of implementations, the sensitivity of a sensor configuration is extended beyond the dynamic range of the piezoresistive material by including multiple piezoresistive components that are spaced at different distances from the conductive traces. According to this approach, the more distant piezoresistive component(s) "take over" when the closer piezoresistive component(s) run out of dynamic range. An example of one such sensor configuration is shown in FIG. 3.

Figure 3:
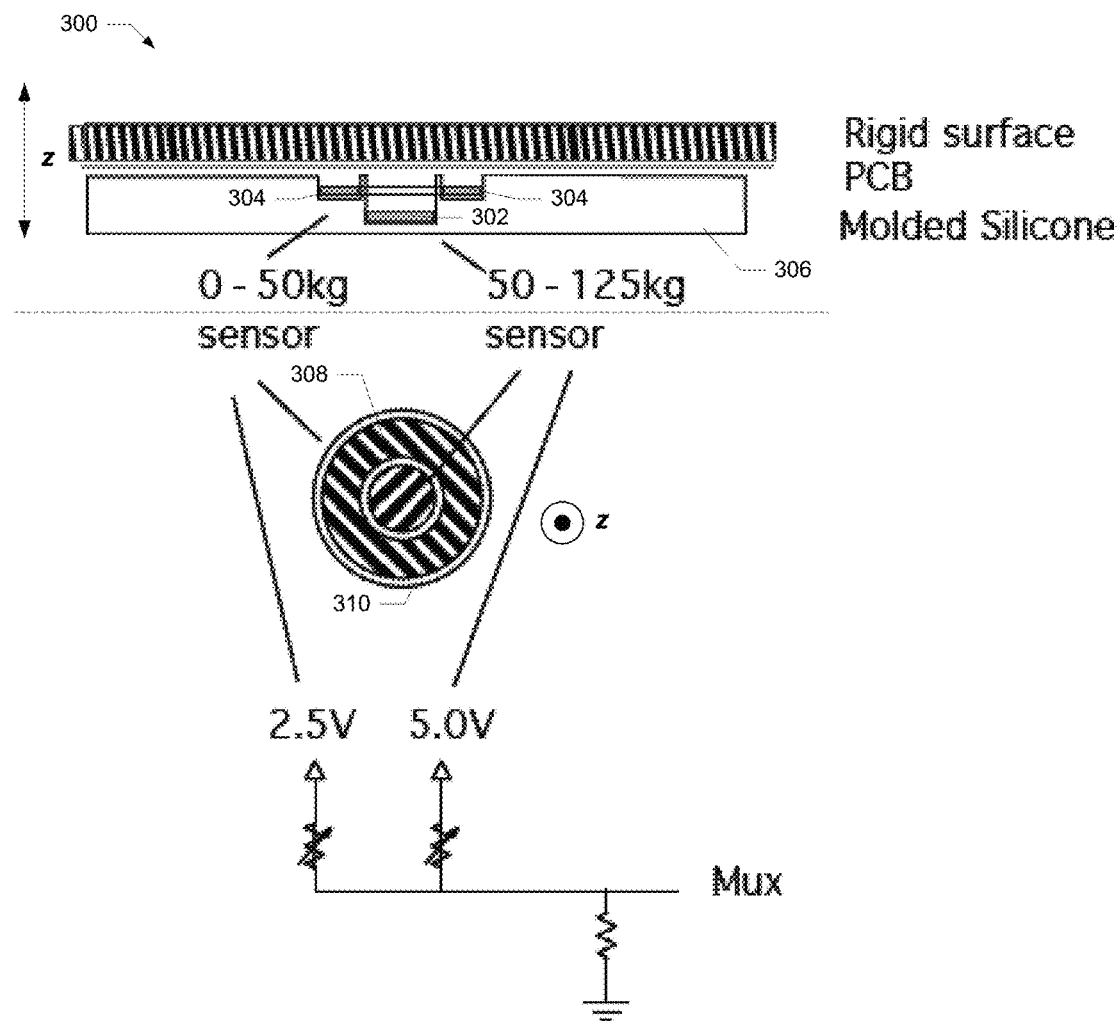
FIG. 3 illustrates yet another sensor configuration.

In sensor 300 of FIG. 3, two distinct piezoresistive components 302 and 304 are supported in a molded silicone structure 306 at different distances from corresponding patterns of conductive traces 308 and 310 on a PCB 312. The piezoresistive components have a concentric configuration (when viewed along the z-axis) in which a circular piezoresistive component is surrounded by an annular piezoresistive component. The conductive traces corresponding to each of the piezoresistive components are arranged as parallel traces in an area similar in shape to the corresponding piezoresistive component. The change in resistance for each set of parallel traces is measured between adjacent traces.

As the silicone in which piezoresistive components 302 and 304 are embedded is compressed, the closer annular component contacts the corresponding conductive traces on the PCB first. As the silicone is further compressed, the more distant circular component then contacts its corresponding conductive traces on the PCB. In the depicted implementation, the silicone and the distances of the piezoresistive components from the PCB are constructed such that the more distant component and the corresponding traces become active around where the closer component and its traces begin to run out of dynamic range. For example, the closer piezoresistive component and the corresponding conductive traces might have a dynamic range covering 0 to about 50 kg of force while the more distant piezoresistive component and its traces might have a dynamic range from about 50 to about 100 kg.

It should be noted that the concentric arrangement of the piezoresistive components and their corresponding trace patterns are merely one example of how multiple components may be configured to achieve a desired dynamic range for a sensor configuration. That is, implementations are contemplated in which the piezoresistive components and their corresponding trace patterns have different shapes and relative arrangements. Implementations are also contemplated in which there are more than two piezoresistive components with corresponding trace patterns. For example, an array might be arranged in a checkerboard pattern in which alternating piezoresistive components and their corresponding trace patterns are configured to cover two or more different parts of the overall dynamic range of the sensor.

Implementations are also contemplated in which the different dynamic ranges associated with the different piezoresistive materials are achieved (at least in part) through variation in the shape, configuration, spacing, and/or conductivity of the different trace patterns. For example, a closely-spaced, dense trace pattern might be used to cover a more sensitive portion of a dynamic range, while a more widely-spaced, sparser trace pattern is used to cover a less sensitive portion of the dynamic range. These types of variations may be done in combination with varying the spacing of the piezoresistive components from the trace patterns and/or the mechanical resistance to applied force of different areas of the sensor.

According to a particular implementation and as shown in FIG. 3, the signals from the multiple piezoresistive components can be read using a shared signal line. In the depicted implementation, the conductive traces corresponding to the closer piezoresistive component covering the lower part of the dynamic range are biased with a lower potential (e.g., 2.5 volts). That is, half of the traces are connected to the lower potential alternating with the other half of the traces being connected to ground via a fixed resistance, as well as providing the output of the sensor (e.g., to an A-to-D converter via a multiplexer). The conductive traces corresponding to the more distant piezoresistive component covering the higher part of the dynamic range are similarly biased with a higher potential (e.g., 5 volts). With this configuration, the dynamic range associated with the closer piezoresistive component (e.g., 304) is represented by the range of 0-2.5 volts, while the dynamic range associated with the more distant piezoresistive component (e.g., 302) is represented by the range of 2.5-5 volts on the same signal line. Reducing the number of signal lines required to acquire this sensor data is advantageous, particularly where there are multiple sensors from which data are acquired.

According to a particular class of implementations, sensors may be implemented using one or more arrays of driven or scanned conductive traces alternating with conductive traces connected to a voltage reference, e.g., ground, through a resistor. Each array is overlaid with a corresponding piezoresistive component. The driven conductive traces in each array are sequentially selected and activated, e.g., by raising its voltage to a known level. When pressure is applied, the driven trace(s) at the point of contact are connected to the adjacent common traces through the piezoresistive material. The voltage at the junction of the common traces and the driven trace(s) is thereby raised. The processor or controller driving the driven traces also sequentially measures the corresponding signal levels to determine whether and where a touch event occurs, and the magnitude of the pressure applied. The processor or controller can also therefore detect the direction and speed of the touch event along the array. As will be appreciated, because of the sequential selection and activation of the traces, such configurations are capable of detecting multiple touch events substantially simultaneously.

Figure 4:
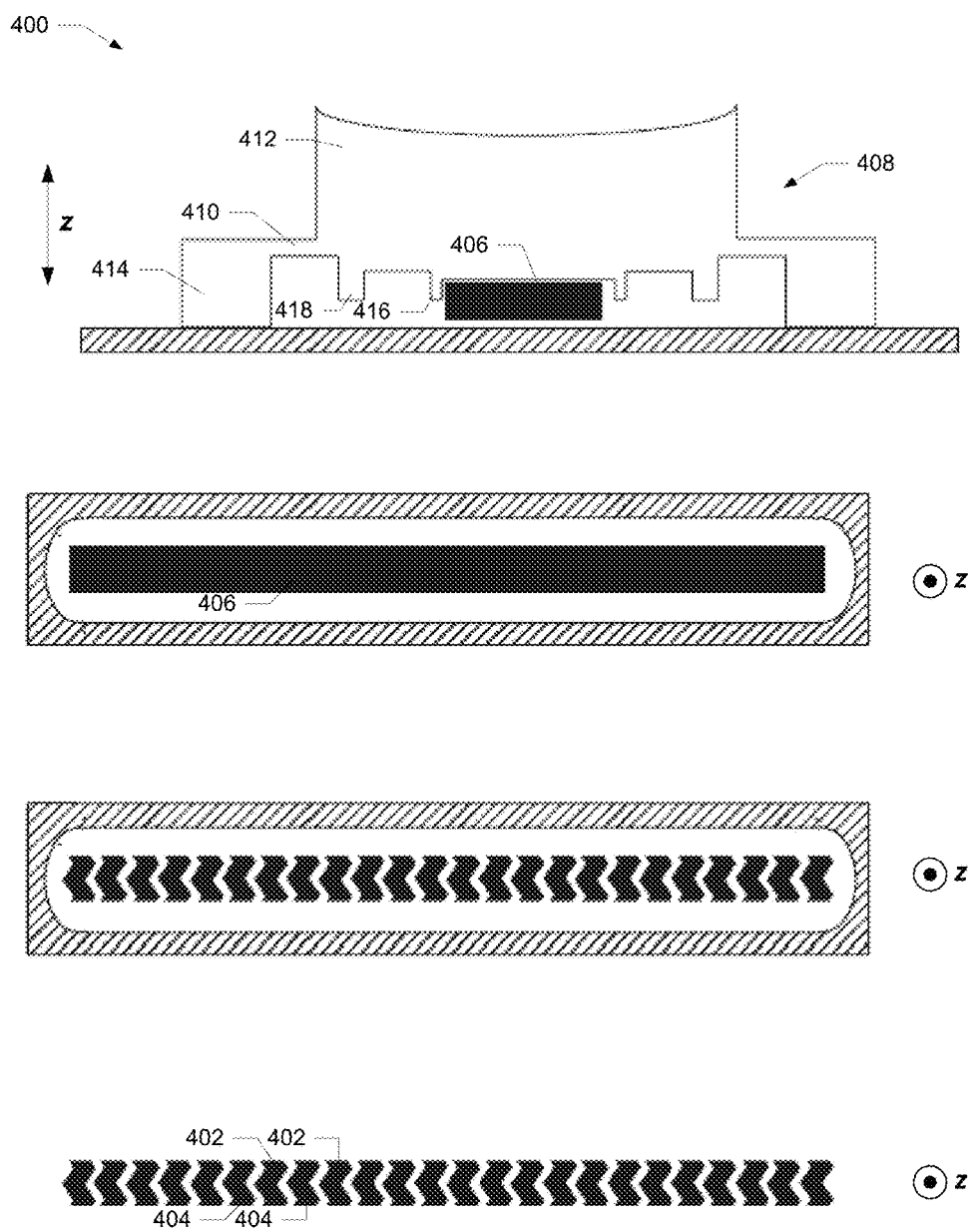
FIG. 4 illustrates still another sensor configuration.
Figure 5:
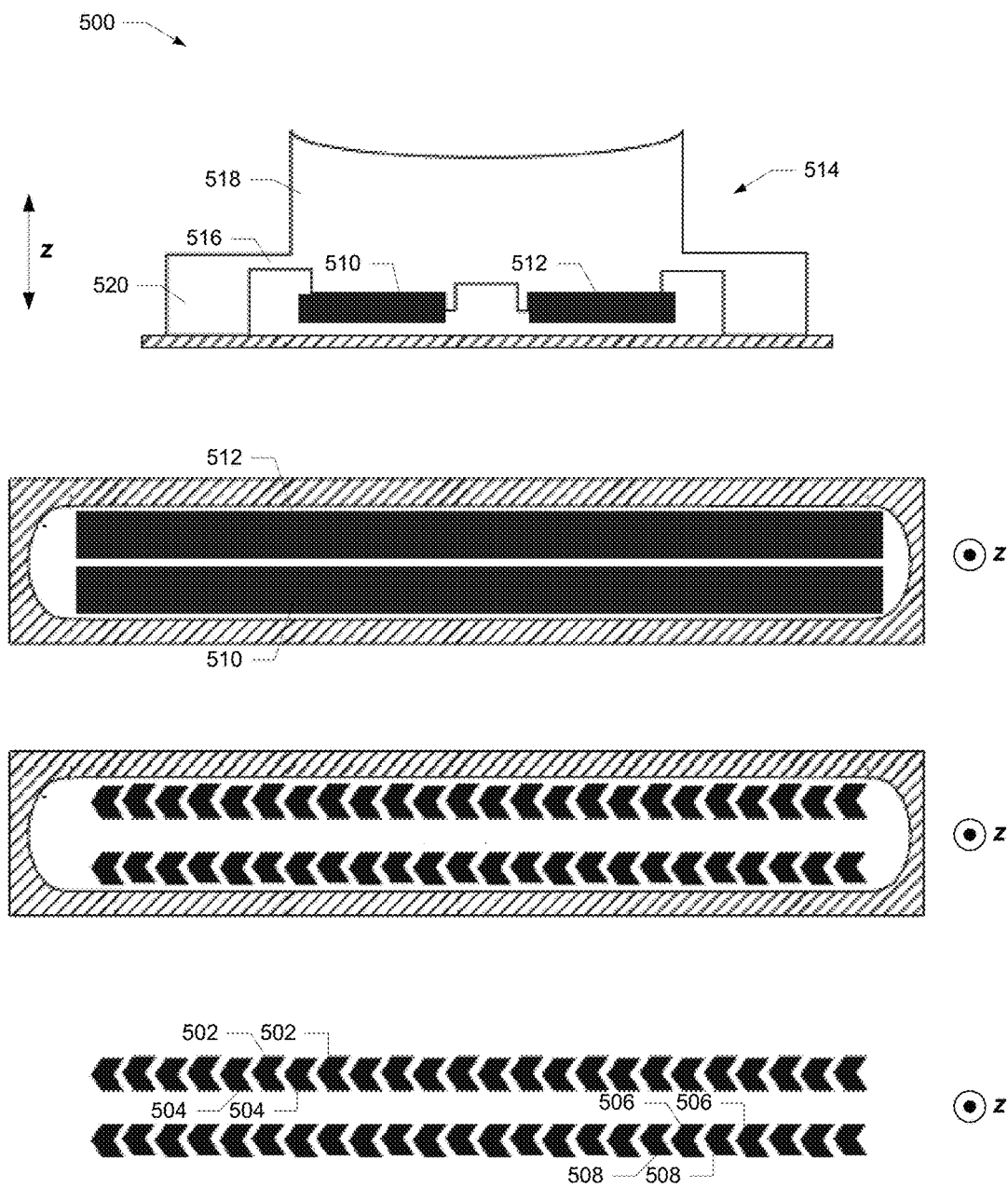
FIG. 5 illustrates a further sensor configuration.

FIG. 4 shows a configuration of such a sensor 400 in which conductive traces 402 and 404 are arranged in a linear array. FIG. 5 shows a configuration 500 in which the conductive traces 502-508 are arranged in two parallel linear arrays. The sensor configurations shown in FIGS. 4 and 5 are designed for use as a fader or slider control with an elongated rectangular key. The linear arrays of conductive traces for each configuration are each aligned with a corresponding piezoresistive component (406 or 510 and 512) supported at a distance from the corresponding traces in a silicone structure (408 or 514). A cantilever structure (410 or 516) in the silicone (i.e., the webbing element that connects and suspends a key part of the structure (412 or 518) to and within a framing part of the structure (414 or 520)) allows it to collapse evenly and easily, bringing the piezoresistive components into contact with the corresponding arrays with very little pressure, e.g., 30-50 grams. The silicone structure may include guides (416) for placement of the piezoresistive components as well as stops (418) that resist the vertical travel of the key. By having two arrays as shown in the configuration of FIG. 5, the associated processor or controller can determine not only the linear location, force, and direction of touch events, but also lateral motion perpendicular to the arrays, e.g., rocking left and right on the key.

According to another class of implementations, conductive traces are printed, screened, deposited, or otherwise formed directly onto flexible piezoresistive material. As will be appreciated, this allows for the creation of a sensor or sensor array that fits any arbitrary shape or volume. The piezoresistive material may be any of a variety of woven and non-woven fabrics having piezoresistive properties. Implementations are also contemplated in which the piezoresistive material may be any of a variety of flexible materials, e.g., rubber, having piezoresistive properties. The conductive traces may be formed using any of a variety of conductive inks or paints. Implementations are also contemplated in which the conductive traces are formed using any flexible conductive material that may be formed on the flexible piezoresistive material. It should therefore be understood that, while specific implementations are described with reference to specific materials and techniques, the scope of this disclosure is not so limited.

Both one-sided and two-side implementations are contemplated, e.g., conductive traces can be printed on one or both sides of the piezoresistive fabric. As will be understood, two-sided implementations may require some mechanism for connecting conductive traces on one side of the fabric to those on the other side. Some implementations use vias in which conductive ink or paint is flowed through the via to establish the connection. Alternatively, metal vias or rivets may make connections through the fabric.

Both single and double-sided implementations may use insulating materials formed over conductive traces. This allows for the stacking or layering of conductive traces and signal lines, e.g., to allow the routing of signal line to isolated structures in a manner analogous to the different layers of a PCB.

Routing of signals on and off the piezoresistive fabric may be achieved in a variety of ways. A particular class of implementations uses elastomeric connectors (e.g., ZEBRA® connectors) which alternate conductive and nonconductive rubber at a density typically an order of magnitude greater than the width of the conductive traces to which they connect (e.g., at the edge of the fabric). Alternatively, a circuit board made of a flexible material (e.g., Kapton), or a bundle of conductors may be riveted to the fabric. The use of rivets may also provide mechanical reinforcement to the connection.

Matching conductive traces or pads on both the piezoresistive material and the flexible circuit board can be made to face each. A layer of conductive adhesive (e.g., a conductive epoxy such as Masterbond EP79 from Masterbond, Inc. of Hackensack, N.J.) can be applied to one of the surfaces and then mated to the other surface. The conductive traces or pads can also be held together with additional mechanical elements such as a plastic sonic weld or rivets. If conductive rivets are used to make the electrical connections to the conductive traces of the piezoresistive fabric, the conductive adhesive may not be required. Conductive threads may also be used to connect the conductive traces of the fabric to an external assembly.

According to a particular class of implementations, the piezoresistive material is a pressure sensitive fabric manufactured by Eeonyx, Inc., of Pinole, Calif. The fabric includes conductive particles that are polymerized to keep them suspended in the fabric. The base material is a polyester felt selected for uniformity in density and thickness as this promotes greater uniformity in conductivity of the finished piezoresistive fabric. That is, the mechanical uniformity of the base material results in a more even distribution of conductive particles when the slurry containing the conductive particles is introduced. Calendared material presents a smoother outer surface which promotes more accurate screening of conductive inks than a non-calendared material. The fabric may be woven. Alternatively, the fabric may be non-woven such as, for example, a calendared fabric e.g., fibers, bonded together by chemical, mechanical, heat or solvent treatment. The conductive particles in the fabric may be any of a wide variety of materials including, for example, silver, copper, gold, aluminum, carbon, etc. Some implementations may employ carbon graphenes that are formed to grip the fabric. Such materials may be fabricated using techniques described in U.S. Pat. No. 7,468,332 for Electroconductive Woven and Non-Woven Fabric issued on Dec. 23, 2008, the entire disclosure of which is incorporated herein by reference for all purposes. However, it should again be noted that any flexible material that exhibits a change in resistance or conductivity when pressure is applied to the material and on which conductive traces may be printed, screened, deposited, or otherwise formed will be suitable for implementation of sensors as described herein.

Conductive particles may be introduced to the fabric using a solution or slurry, the moisture from which is then removed. According to some implementations, the way in which the moisture is removed from the fabric may also promote uniformity. For example, using an evenly distributed array of vacuum heads or ports to pull the moisture from the fabric reduces the concentrations of conductive particles around individual vacuum heads or ports. The vacuum heads or ports may be arranged in 1 or 2 dimensional arrays; the latter being analogized to a reverse air hockey table, i.e., an array of vacuum ports which pull air in rather than push air out.

Implementations are also contemplated in which the uniformity of the piezoresistive fabric is not necessarily very good. Such implementations may use multiple, closely-spaced sensors operating in parallel, the outputs of which can be averaged to get more accurate and/or consistent readings.

According to a particular class of implementations, conductive traces having varying levels of conductivity are formed on the piezoresistive material using conductive silicone-based inks manufactured by, for example, E.I. du Pont de Nemours and Company (DuPont) of Wilmington, Del., and/or Creative Materials of Ayer, Mass. An example of a conductive ink suitable for implementing highly conductive traces for use with various implementations is product number 125-19 from Creative Materials, a flexible, high temperature, electrically conductive ink. Examples of conductive inks for implementing lower conductivity traces for use with various implementations are product numbers 7102 and 7105 from DuPont, both carbon conductive compositions. Examples of dielectric materials suitable for implementing insulators for use with various implementations are product numbers 5018 and 5036 from DuPont, a UV curable dielectric and an encapsulant, respectively. These inks are flexible and durable and can handle creasing, washing, etc. The degree of conductivity for different traces and applications is controlled by the amount or concentration of conductive particles (e.g., silver, copper, aluminum, carbon, etc.) suspended in the silicone. These inks can be screen printed or printed from an inkjet printer. Another class of implementations uses conductive paints (e.g., carbon particles mixed with paint) such as those that are commonly used for EMI shielding and ESD protection.

Figure 6:
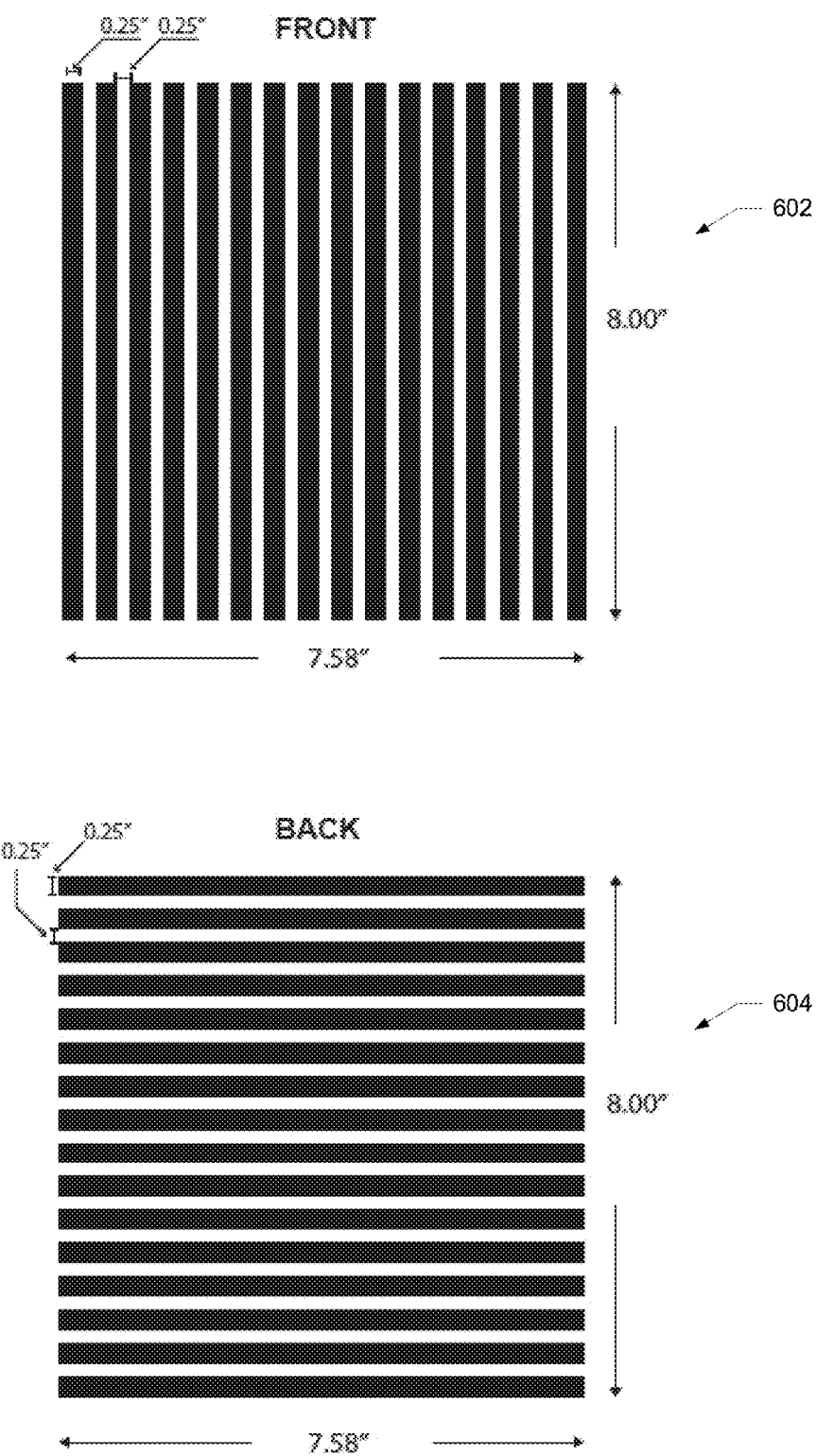
FIG. 6 illustrates a two-sided sensor array.

One example of a two-sided implementation is shown in FIG. 6 and has an array 602 of parallel conductive traces oriented in one direction printed on one side of the piezoresistive fabric, and another array 604 oriented at 90 degrees to the first array printed on the other side of the fabric. This implementation takes advantage of the fact that the piezoresistive fabric is conductive through its thickness (in addition to laterally and across its surface) to implement a pressure sensitive X-Y matrix. By sequentially driving the array on one side of the piezoresistive material and sequentially scanning the array on the other side, both the position and force of a touch event on the array can be detected. Again, because of the sequential selection and activation of the traces, such a configuration is capable of detecting multiple touch events substantially simultaneously. As will be understood, the applications for such a sensor array are virtually limitless.

As will be understood by those of skill in the art, a variety of techniques may be employed to acquire data from sensors constructed as described herein. Some of these techniques may involve a simple measurement of a change in resistance (as determined from a voltage or current) between two conductive traces having the same or similar conductivity. However, for sensors having arrays that include many conductive traces, this may require an unacceptable number of signal lines to route signals both to and from the sensor array. Therefore, according to a particular class of implementations, conductive traces formed on piezoresistive material and having different levels of conductivity are driven and interrogated with signal patterns that reduce the number of signal lines required to achieve sensor configurations that are sensitive to location, pressure, direction, and velocity of applied force.

FIG. 7 illustrates an example of such an implementation intended to provide functionality similar to the sensor of FIG. 5 but with many fewer signal lines. Adjacent (in this case substantially parallel) conductive traces are formed on piezoresistive fabric 700 with one (E) being highly conductive, e.g., near-zero resistance, and the other (AB) being less conductive, e.g., about 100 ohms from A to B if the resistance between traces AB and E without pressure is about 1K ohms. The less conductive trace is driven at opposing ends by different signals A and B (e.g., by one or more signal generators). Pressure on the piezoresistive material reduces the resistance between the two traces which, depending on the location, results in different contributions from signals A and B measured in a mixed signal on the highly conductive trace E. The overall amplitude of the mixed signal also increases with pressure.

According to a particular class of implementations, signals A and B are different pulse trains of the same amplitude; e.g., one at 1 kHz, one with a 50% duty cycle, and the other at 500 Hz with a 75% duty cycle as shown in FIG. 7. The phases of the two pulse trains are synchronized to avoid zero volts being applied to the less conductive trace. Location information can be derived from the mixed signal measured on E as follows. The signal on E is sampled by an A/D converter (e.g., oversampled by a factor of two or more relative to the frequency of the inputs). An inexpensive, general-purpose processor may be employed that can read up to 40 signals with up to 10-bits of resolution, and take 500K samples per second. The same general processor may drive the conductive traces. Thus, arrays with large numbers of sensors may be constructed relatively inexpensively.

The processor evaluates specific amplitudes at specific times that are correlated with the values of signals A and B at those times. The relative contribution from each signal is determined by selecting closely-spaced samples of the mixed signal at times when the respective signals are each known to have a particular value or characteristic, e.g., full amplitude. The ratio of those two measurements represents the relative contributions of each signal to the mixed signal that, in turn, can be mapped to a location between the end points of the AB trace. The pressure or force of the touch event can be determined by measuring peak values of the sampled mixed signal. With this configuration, a pressure sensitive slider can be implemented with only 3 signal lines required to drive the traces and acquire the signal (as opposed to the many signal lines associated with the linear array of traces in sensor configuration of FIG. 5.

According to a particular implementation shown in FIG. 7, a second conductive trace CD runs parallel to trace E on the opposing side from trace AB. As with trace AB, the opposing ends of this additional conductive trace are driven with signals C and D; each different from the other as well as signals A and B. As a result, the mixed signal on trace E includes contributions from each of the four signals. This mixed signal may be processed for one or both of the signal pairs in a manner similar to that described above to determine the location of a touch event along the longitudinal axis of the array. The relative amplitudes of the two signal pairs (e.g., derived by measuring amplitudes for the combination of signals A and B and the combination of signals C and D) represent the location of the touch event along the latitudinal axis of the array. This enables measuring of the location of the touch event in two dimensions. This might enable, for example, the capture of a sideways rocking motion of a finger on a key. As with the example described above, the pressure of the touch event may be determined by measuring peak values of the sampled mixed signal. In this way, an XYZ sensor may implemented with five traces (with the Z axis being represented by the force of the touch event).

Figure 8:
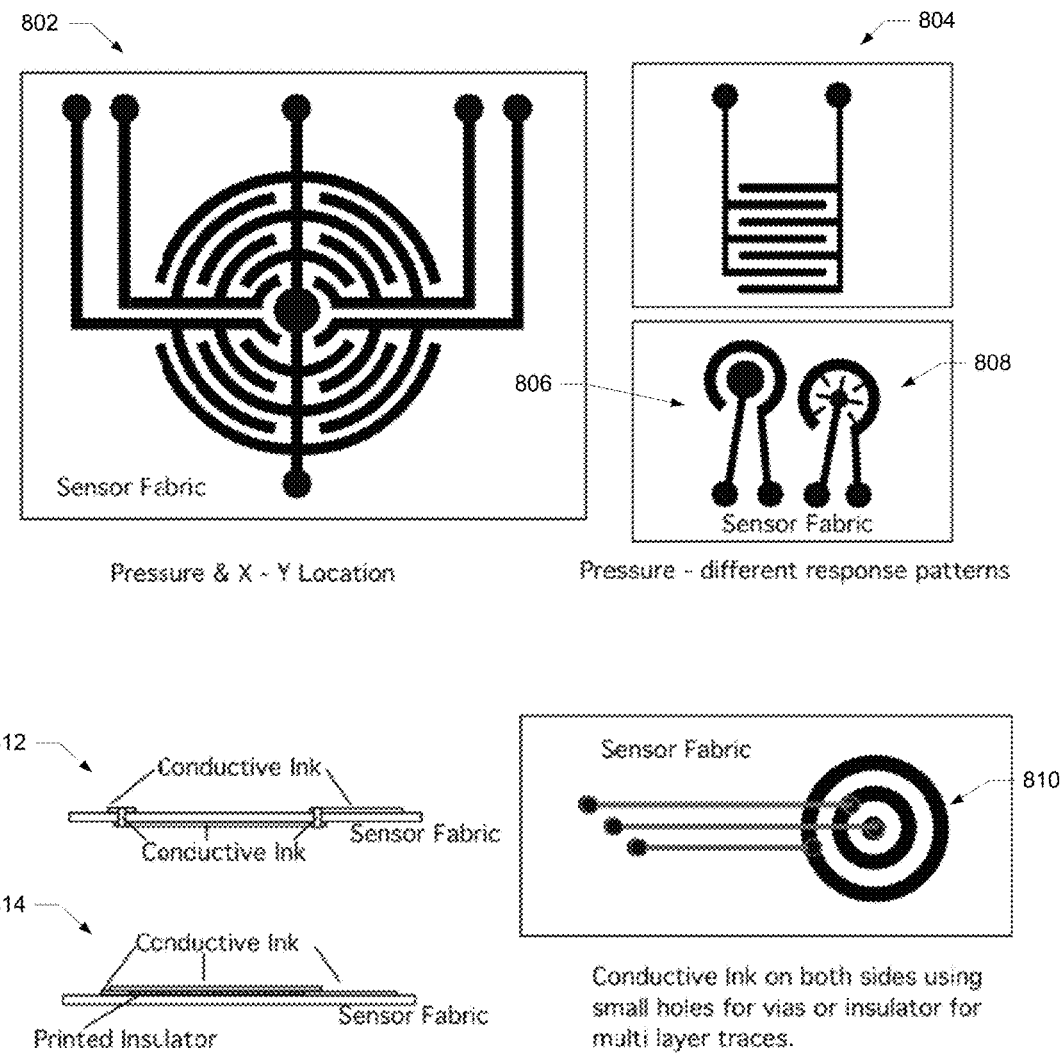
FIG. 8 illustrates various sensor configurations.

FIG. 8 shows a variety of trace patterns formed on flexible piezoresistive material, e.g., conductive ink on piezoresistive fabric, for different applications. Trace pattern 802 implements a four-quadrant sensor that operates similarly to those described, for example, in U.S. Pat. No. 8,680,390 and U.S. Patent Publication No. 2013/0239787, incorporated herein by reference above. In addition to detecting the occurrence and force of touch events, such a sensor may also be configured to determine the direction and velocity of motion over the quadrants including, for example, both linear and rotational motion relative to the surface of the sensor. Trace patterns 804, 806 and 808 implement sensors that measure the occurrence and force of touch events with different response curves and dynamic ranges resulting from the different configurations.

Trace pattern 810 is used to illustrate both single and double-sided implementations that use either vias or rivets through the piezoresistive material (e.g., configuration 812), insulating materials formed over conductive traces (e.g., configuration 814), or both. As discussed above, such mechanisms enable complex patterns of traces and routing of signals in a manner analogous to the different layers of a PCB.

Figure 9:
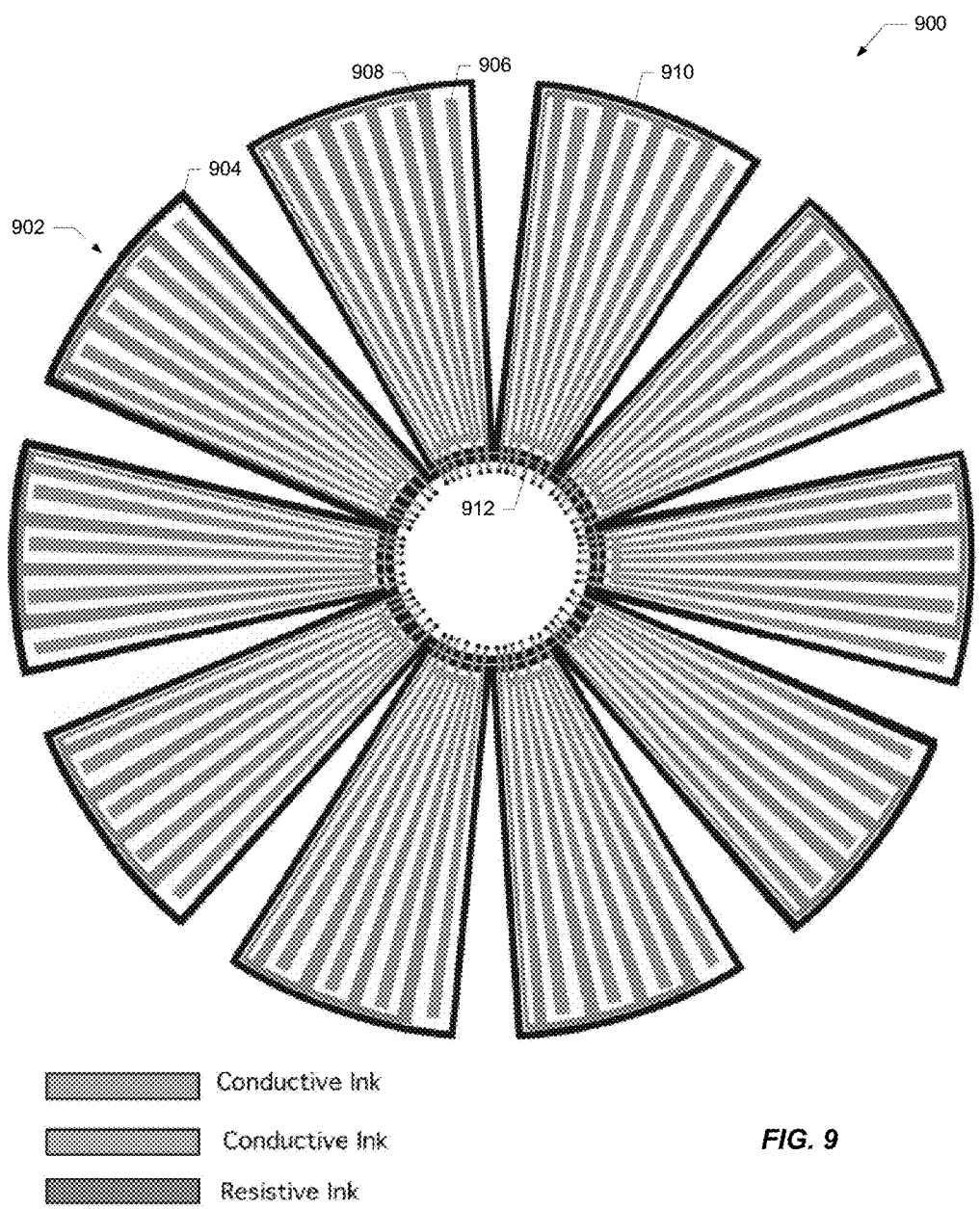
FIG. 9 illustrates a hemispherical sensor array.

FIG. 9 illustrates a sensor array 900 for inclusion in a helmet or skull cap worn on a human head, e.g., for measuring the force and location of impacts. Such an array might be suitable, for example, for capturing data regarding contact events on sports helmets or other protective gear designed to protect the human head. This information might be useful during the design and testing phases of such protective gear, as well as gathering data once in use. It should be noted that sensors located in a cap that covers areas of the skull provide information about contact events that actually reach the skull. This is to be contrasted with some existing systems that instead measure the contact event to the protective helmet. Each flap 902 is constructed from a flexible piezoresistive material 904 with a pattern of conductive traces formed on the material, e.g., conductive ink printed on piezoresistive fabric. As with the traces of FIG. 7, some of the traces 906 are highly conductive and alternate with traces 908 having lower conductivity.

Like trace AB of FIG. 7, traces 908 on each flap are driven at opposing ends with signals having the same amplitude and different duty cycles. The same pair of signals may be used for all of the flaps. These signals are routed to the opposing ends of traces 908 from the center of the array via traces 910 and 912. As can be seen, trace 912 on each flap crosses over traces 906 from which trace 912 is insulated, e.g., from insulators (not shown) printed or formed over the underlying conductive traces.

Each of the signals on traces 906 is routed to the center of the array and represents the mixing of the signals on adjacent traces 908. The location and magnitude of touch events along longitudinal axes of the traces (e.g., the radial coordinate from the center of the array) may be determined from the mixed signal as described above with reference to FIG. 7. The angular coordinate may be determined from the conductive trace 906 that registers the touch event.

Figure 10:
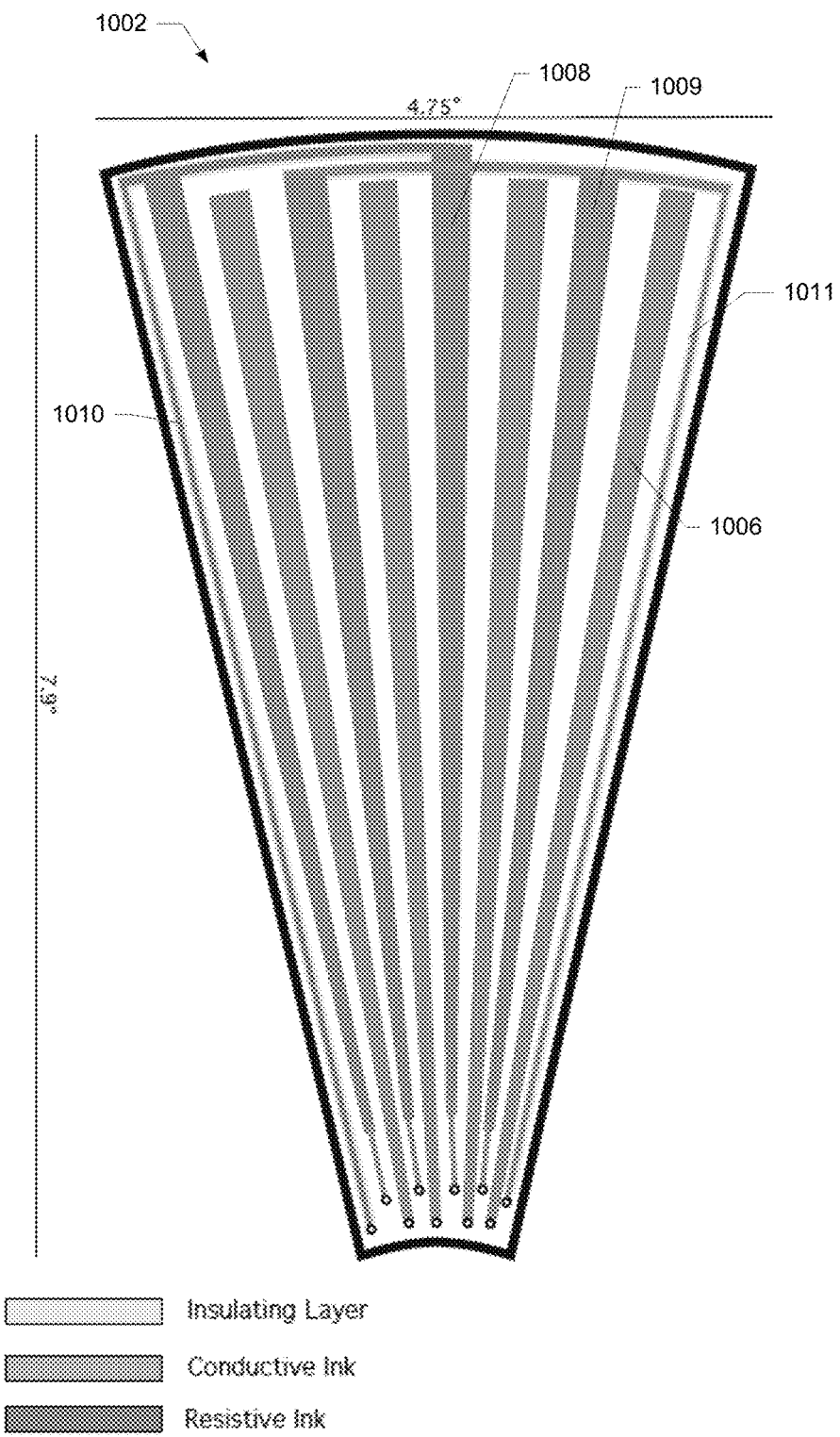
FIG. 10 illustrates a portion of a hemispherical sensor array.

An alternative implementation of the flap for such a sensor array similar to the one depicted in FIG. 9 is shown in FIG. 10. Flap 1002 includes an alternating pattern of highly conductive traces 1006 and traces 1008 and 1009, both of which are characterized by a lower conductivity than traces 1006. However, instead of driving each of the lower conductivity traces with the same signal pair as described above with reference to FIG. 9, traces 1008 are driven with one signal pair (using trace 1010) and traces 1009 are driven with another (using traces 1011). This is analogous to the addition of the second conductive trace CD described above with reference to FIG. 7. That is, the mixed signals present on each of traces 1006 can be processed as described above with reference to the configuration of FIG. 7 to determine the relative contributions from the 4 signals driving adjacent traces 1008 and 1009, and therefore the location of an applied force in two dimensions, e.g., along the longitudinal axes of the traces (the radial coordinate from the center of the array), and the latitudinal axes of the traces (the angular coordinate relative to the center of the array). The magnitude of the applied force may also be determined as described above with reference to FIG. 7.

Figure 11:
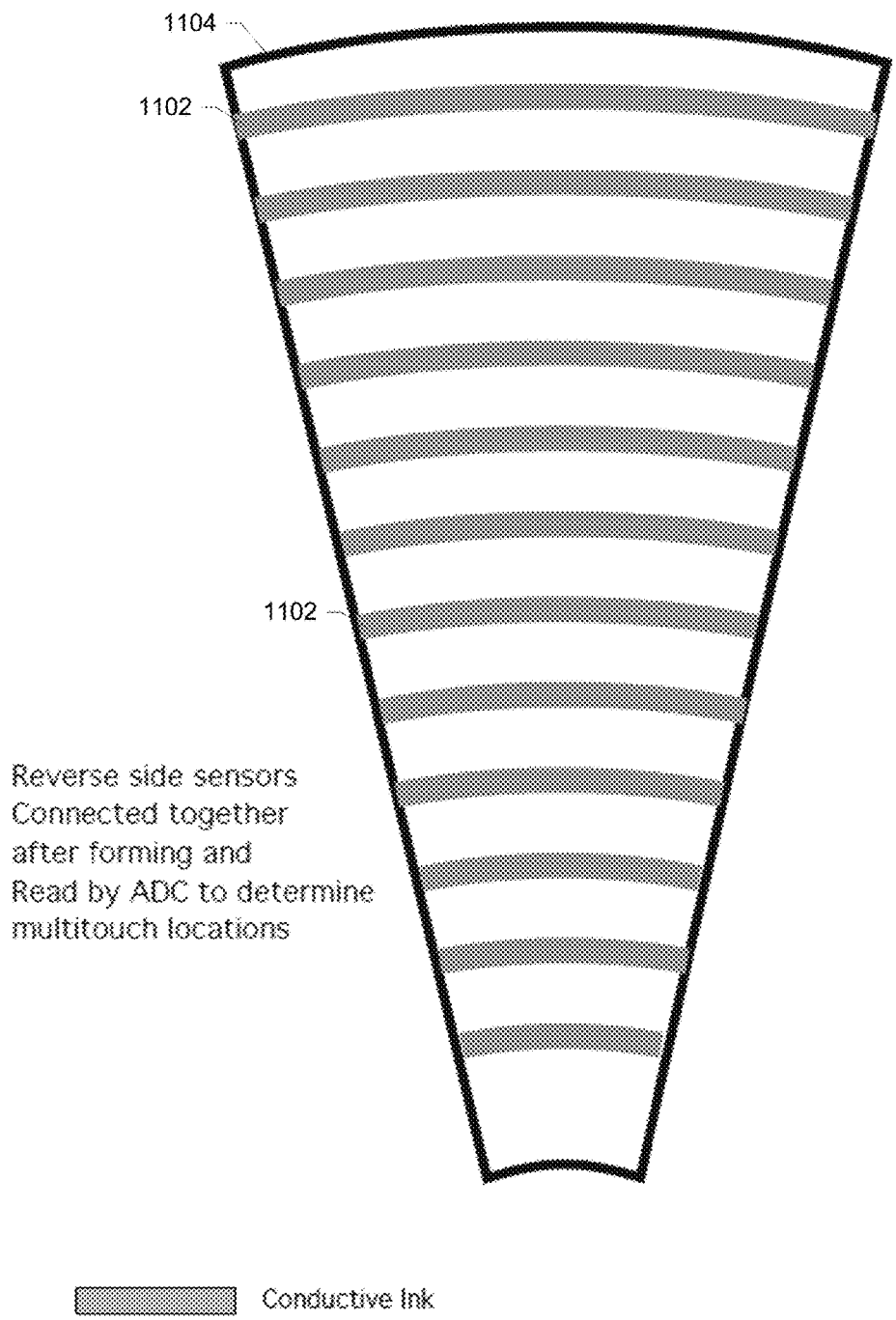
FIG. 11 illustrates a portion of a hemispherical sensor array.

FIG. 11 illustrates a pattern of conductive traces 1102 on a flap 1104 that may be on the other side of the flap from the trace patterns of FIG. 9 or 10. Traces 1102 may be used in conjunction with the techniques described above to disambiguate between multiple simultaneous touch events. For example, as discussed above, the mixed signals on traces 1006 of FIG. 10 include contributions from adjacent traces 1108 and 1109 as affected by the location and magnitude of an applied force or touch event. However, if there were two simultaneous touch events on the same flap, there would be ambiguity as to the locations of the events as the mixing of the resulting signals would, in effect, perform a kind of averaging that would result in a reading that doesn't accurately represent the location of either event. Traces 1102 on the other side of the flaps may be configured to address this issue.

According to a particular implementation in which multiple flaps 1104 are configured as shown in FIG. 9, a roughly hemispherical shape may be formed by bringing the long edges of the flaps together. Traces 1102 can be connected to corresponding traces on adjacent flaps to form something analogous to latitude lines around the hemisphere. Signals on each of these traces can be read (e.g., by an analog-to-digital converter (ADC) and an associated processor) to identify the places of activity on the opposite side of the fabric. For example if two pressure points are along the same longitudinal trace on the other side of the fabric (e.g., traces 1006) they may not be distinguishable. However, by examining the latitudinal traces it can be determined where the points of contact are based upon increased signal level present. Locations between the latitudinal traces can be determined using relative signal strength.

As will be appreciated, the sampling rate of the latitudinal conductors may be sufficiently fast to detect multiple touch events at different latitudes substantially simultaneously. As will also be appreciated, if the traces 1102 on all of the flaps are connected as described, the information derived from these traces will only give a latitude for each of the multiple touch events. However, this can be combined with information derived from traces on the other side of the flaps (e.g., as discussed above with reference to FIGS. 9 and 10) to determine the longitudinal (e.g., east to west) coordinates of the events. In an alternative implementation, traces 1102 on each flap may be processed independently of the other flaps with the introduction of additional signal lines.

As mentioned above, the description of specific implementations herein is intended to provide illustrative examples rather than limit the scope of this disclosure. And although two classes of sensors have been described herein, it should be understood that at least some of the techniques and configurations described may be employed by either class of sensor. For example, the technique for driving and reading conductive traces described above with reference to FIG. 7 is not limited to implementations in which the conductive traces are formed on the piezoresistive material. That is, the same principle may be applied to the class of sensors in which piezoresistive material is supported (e.g., within a silicone key or control pad) adjacent conductive traces that are arranged on a substrate (e.g., a printed circuit board (PCB)) rather than formed directly on the piezoresistive material. An example of such an implementation is illustrated in FIG. 12.

In the depicted implementation, trace E (which may be, for example, copper) is formed on PCB 1202 with two adjacent and parallel traces AB and CD (which may be, for example, printed ink resistors). The resistance of trace E is near zero. For some applications, the resistance of traces AB and CD may be about 10% of the relaxed surface resistance of piezoresistive material 1204 over the distance between those traces and trace E. Piezoresistive material 1204 is held adjacent the three traces in a compressible structure 1206 (which may be, for example, silicone). Piezoresistive material 1204 may be held at a distance from the traces or in contact with them.

As described above with reference to FIG. 7, four unique signals A, B, C and D drive the corresponding ends of traces AB and CD. The resulting mixed signal on trace E may then be processed to determine the location, direction, velocity and force of a touch event on the surface of structure 1206.

For implementations that employ arrays of sensors and/or in which the magnitude of applied forces captured by sensors is important, the uniformity of the piezoresistive material can be critical. Therefore, a class of test systems is provided that is configured to measure changes in resistance of a piezoresistive material at a number of closely spaced locations. According to a particular subclass of test systems, an array of conductive traces is provided on a substantially rigid substrate such as, for example, a printed circuit board (PCB). A sheet of piezoresistive material (e.g., a piezoresistive fabric as described herein) to be tested is placed over the PCB in contact with the conductive traces, and pairs of the conductive traces are sequentially activated such that the signals representative of the resistance of the piezoresistive material are captured at an array of locations (e.g., by associated circuitry on the PCB). By introducing known forces on the piezoresistive material, the response of the piezoresistive material may be characterized over its surface and/or volume, thus yielding test data representing how uniformly the material behaves in response to applied force.

As will be appreciated, such information would be extremely useful for manufacturers of piezoresistive materials in designing and evaluating new materials as well as classifying products with regard to their uniformity characteristics. Such information would also be useful to designers of systems incorporating such materials (e.g., sensor systems) in that they will be able to select materials that have a level of uniformity that is appropriate for their particular application.

An example of such a test system 1300 is shown in FIG. 13. Pairs of interlaced conductive traces 1302 and 1304 are formed on a PCB to provide an array of 256 locations at which the resistance of a sheet of piezoresistive material placed in contact with the array (not shown) may be measured. As will be appreciated the number of locations, the arrangement of the array, and the configuration of the conductive traces may vary significantly (e.g., see examples described above) for different implementations depending on a number of factors such as, for example, the dynamic range required, the shape, size, and/or construction of the piezoresistive material to be tested, etc. The Simplified Block Diagram included in FIG. 13 illustrates the connection and control of each pair of traces. Trace 1302 is connected to ground (GND). Trace 1304 is pulled up to a bias voltage (VBIAS) of 3.3 volts via a variable impedance and is also the trace by which the resistance measurement of the material under test at that location of the array is made.

Control circuitry 1306 (which may include, for example, a central processing unit (CPU) and associated circuitry) sequentially reads the signals at each of traces 1304 in the array by controlling multiplexers 1308. The measurements are digitized and serialized and transmitted to a computing device, e.g., a desktop or laptop computer, a tablet, a smart phone, etc. (not shown), via USB port 1310. As will be appreciated, similar conversion and processing circuitry may be used with any of the sensor configurations described herein. As force is exerted on a piezoresistive material under test in contact with a particular pair of traces, the resistance of the material (represented by variable resistor 1312) changes, and the resulting signal is captured by control circuitry 1306. According to some implementations, additional structures may be formed on the PCB as a counterbalance to the conductive traces to better maintain the flatness of the PCB. These might be, for example, non-conductive traces or additional conductive traces that have no electrical connections.

Figure 14:
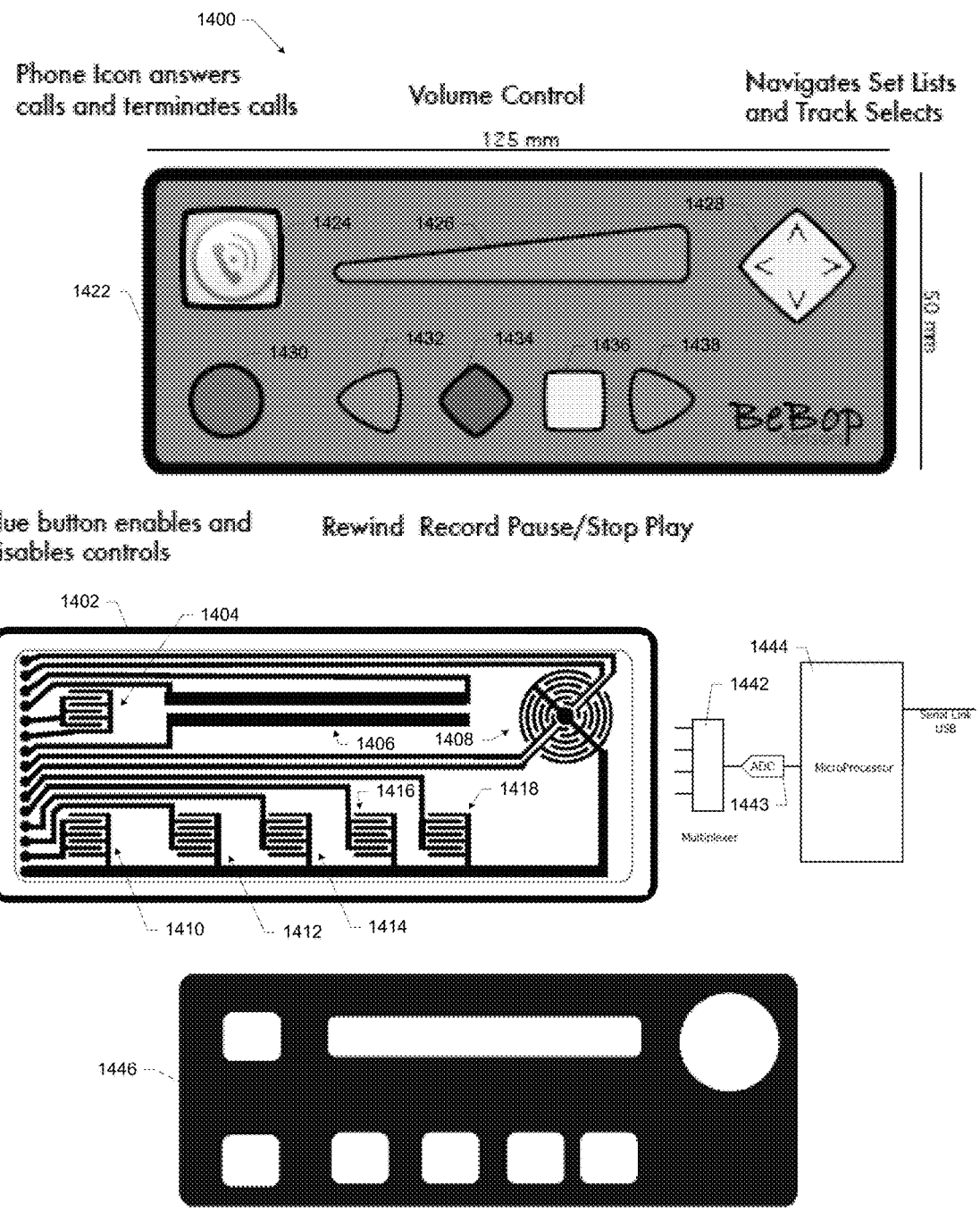
FIG. 14 illustrates a controller that employs a variety of sensor configurations.

It will be appreciated that sensors and sensor arrays designed as described in this disclosure may be employed in a very broad and diverse range of applications in addition to those described. One example of such an application is a controller 1400 for a smart phone or a digital media player as shown in FIG. 14. Controller 1400 may be implemented with an underlying piezoresistive substrate 1402 with conductive traces patterns 1404-1418 formed directly on the substrate to implement sensors that provide different types of controls. The trace patterns are aligned with a particular icon representing the control on an overlying substrate 1422 with which a user interacts (i.e., icons 1424-1438). Alternatively, trace patterns 1404-1418 may be formed on the opposite side of the same substrate from icons 1424-1438. The substrate(s) from which controller 1400 is constructed may be a piezoresistive fabric that may be incorporated, for example, in articles of clothing, e.g., in the sleeve of a shirt or jacket.

As described elsewhere herein, when pressure is applied to one of the controls, a resulting signal may be digitized and mapped by associated processing circuitry (e.g., multiplexer 1442, A-D converter 1443, and processor 1444) to a control function associated with a connected device, e.g., the smart phone or media player (not shown) via, for example, a USB connection. As will be appreciated, similar conversion and processing circuitry may be employed with any of the sensor configurations described herein. In the depicted implementation, trace pattern 1404 corresponds to icon 1424 and implements a button control that allows the user to answer or terminate calls on his smart phone. Trace pattern 1406 corresponds to icon 1426 and implements a slider (such as the one described above with reference to FIG. 7) for volume control of, for example, a media player. Trace pattern 1408 corresponds to icon 1428 and implements a four-quadrant sensor that may be used for navigation of, for example, set lists, track queues, etc. Trace pattern 1410 corresponds to icon 1430 and implements an enable/disable control by which controller 1400 may be enabled and disabled. Trace patterns 1412-1418 correspond to icons 1432-1438, respectively, and implement various media player controls such as, for example, play, pause, stop, record, skip forward, skip back, forward and reverse high-speed playback, etc. As will be appreciated, this is merely one example of a wide variety of controllers and control functions that may be implemented in this manner.

According to a particular implementation, an insulating layer 1446 may be printed or deposited on piezoresistive substrate 1402 before any of trace patterns 1404-1418. As can be seen, openings in insulating layer 1446 line up with the portions of the trace patterns intended to implement the corresponding control functions. These portions of the trace patterns are therefore printed or deposited directly on the underlying piezoresistive substrate. By contrast, the conductive traces that connect these portions of the trace patterns to the edge of the piezoresistive substrate for routing to the processing circuitry are printed or deposited on insulating layer 1446. This will significantly reduce crosstalk noise between these conductors relative to an approach in which they are also printed on the piezoresistive substrate.

While various specific implementations have been particularly shown and described, it will be understood by those skilled in the art that changes in the form and details of the disclosed implementations may be made without departing from the spirit or scope of this disclosure. In addition, although various advantages, aspects, and objects have been discussed herein with reference to various implementations, it will be understood that the scope of this disclosure should not be limited by reference to such advantages, aspects, and objects.

What is claimed is:

1. A sensor system, comprising:
   piezoresistive fabric;
   a plurality of sensor traces printed, screened, or deposited directly on one or more surfaces of the piezoresistive fabric, the plurality of sensor traces and the piezoresistive fabric forming a plurality of sensors, each of the sensors including two or more of the sensor traces, the sensor traces of each sensor being on a same surface of the piezoresistive fabric;
   first insulating material printed, screened, or deposited directly on one or more of the surfaces of the piezoresistive fabric; and
   a plurality of routing traces printed, screened, or deposited on the first insulating material and connected to corresponding ones of the sensor traces;
   wherein resistance between the sensor traces varies with force applied to the piezoresistive fabric.

2. The sensor system of claim 1, wherein the piezoresistive fabric is woven or non-woven.

3. The sensor system of claim 1, wherein the sensor traces comprise conductive ink printed on the piezoresistive fabric.

4. The sensor system of claim 3, wherein the conductive ink comprises a silicone ink having conductive particles suspended therein.

5. The sensor system of claim 1, wherein the sensor traces comprise conductive paint deposited on the piezoresistive fabric.

6. The sensor system of claim 1, wherein the sensor traces are only on one side of the piezoresistive fabric.

7. The sensor system of claim 1, wherein the sensor traces are on both sides of the piezoresistive fabric.

8. The sensor system of claim 7, wherein a first one of the sensor traces on one side of the piezoresistive fabric is electrically connected to a first one of the routing traces on an opposing side of the piezoresistive fabric using a via through which conductive material is flowed, using a metal via, or using a metal rivet.

9. The sensor system of claim 1, further comprising second insulating material formed over a first one of the routing traces, wherein at least a portion of a second one of the routing traces is formed over the second insulating material and the first routing trace.

10. The sensor system of claim 1, wherein at least some of the sensor traces are electrically connected via corresponding ones of the routing traces to corresponding conductors in a connector at an edge of the piezoresistive fabric.

11. The sensor system of claim 10, wherein the connector comprises an elastomeric connector that alternates conductive and non-conductive rubber, a flexible circuit board, conductive threads configured for connection to an external assembly, or a bundle of conductors connected to the piezoresistive fabric with a conductive adhesive and/or rivets, the conductive adhesive and/or rivets making electrical connections to the routing traces.

12. The sensor system of claim 1, wherein a first sensor trace of a first sensor is characterized by a first conductivity and a second sensor trace of the first sensor is characterized by a second conductivity lower than the first conductivity, the sensor system further comprising circuitry configured to drive one end of the second sensor trace with a first signal characterized by a first duty cycle, and to drive an opposing end of the second sensor trace with a second signal characterized by a second duty cycle, the circuitry being further configured to receive a mixed signal from the first sensor trace, the mixed signal including contributions from the first and second signals via the piezoresistive fabric, the circuitry being further configured to detect a location of a touch event along a first axis of the second sensor trace with reference to the contributions of the first and second signals to the mixed signal.

13. The sensor system of claim 12, wherein the first sensor includes a third sensor trace characterized by the second conductivity, wherein the circuitry is further configured to drive one end of the third sensor trace with a third signal characterized by a third duty cycle, and to drive an opposing end of the third sensor trace with a fourth signal characterized by a fourth duty cycle, wherein the mixed signal includes contributions from the third and fourth signals via the piezoresistive fabric, and wherein the circuitry is further configured to detect the location of the touch event along a second axis of the second and third sensor traces with reference to the contributions of the third and fourth signals to the mixed signal.

14. The sensor system of claim 1, further comprising circuitry configured to receive one or more signals from the sensor traces via the routing traces, and to detect a touch event with reference to the one or more signals.

15. The sensor system of claim 14, wherein the circuitry is further configured to determine either or both of a location of the touch event, and a magnitude of force of the touch event.

16. The sensor system of claim 1, wherein the sensor traces of a first sensor are arranged in quadrants, the sensor system further comprising circuitry configured to detect a touch event with reference to signals received from the sensor traces of the first sensor via the routing traces, the circuitry being further configured to determine a location of the touch event, a magnitude of force of the touch event, a speed of motion of the touch event, and a direction of motion of the touch event.

17. The sensor system of claim 1, further comprising circuitry configured to receive one or more signals from each of the sensors via the routing traces and to generate control information in response thereto, the control information being for controlling operation of one or more processes or devices in communication with the circuitry.

18. An article of clothing including the sensor system of claim 17, wherein the piezoresistive fabric is incorporated into the article of clothing.

19. The sensor system of claim 1, wherein the piezoresistive fabric is one or more pieces of piezoresistive fabric integrated with a cap for wearing on a human head, each of the pieces of piezoresistive fabric having an array of the sensor traces thereon, the sensor system further comprising circuitry configured to detect a touch event with reference to signals received from the sensor traces via the routing traces, the circuitry being further configured to determine a location of the touch event and a magnitude of force of the touch event.

20. The sensor system of claim 19, the array of sensor traces on each of the pieces of piezoresistive fabric includes first sensor traces characterized by a first conductivity alternating with second sensor traces characterized by a second conductivity lower than the first conductivity, the circuitry being configured to drive one end of each of the second sensor traces with a first signal characterized by a first duty cycle, and to drive an opposing end of each of the second sensor traces with a second signal characterized by a second duty cycle, the circuitry being further configured to receive a mixed signal from each of the first sensor traces, the mixed signal including contributions from the first and second signals on adjacent second sensor traces via the piezoresistive fabric, the circuitry being further configured to detect a location of a touch event along a first axis of the second sensor traces with reference to the contributions of the first and second signals to the mixed signal.

21. The sensor system of claim 20, wherein the sensor traces include an array of parallel traces on each of the pieces of piezoresistive fabric oriented substantially perpendicular to the first axis of the second sensor traces, the circuitry being further configured to disambiguate between multiple touch events on a same piece of piezoresistive fabric with reference to signals received from the array of parallel traces.

22. A sensor system, comprising:
piezoresistive fabric;
a plurality of sensor traces printed, screened, or deposited directly on one or more surfaces of the piezoresistive fabric, the plurality of sensor traces and the piezoresistive fabric forming a plurality of sensors, the sensor traces comprising silicone ink having conductive particles suspended therein, each of the sensors including two or more of the sensor traces, the sensor traces of each sensor being on the same side of the piezoresistive fabric;

first insulating material printed, screened, or deposited directly on one or more of the surfaces of the piezoresistive fabric; and a plurality of routing traces printed, screened, or deposited on the first insulating material and connected to corresponding ones of the sensor traces; and circuitry configured to receive one or more signals from the sensor traces via the routing traces, to detect a touch event with reference to the one or more signals, and to determine either or both of a location of the touch event, and a magnitude of force of the touch event.

23. The sensor system of claim 22, wherein the sensor traces are only on one side of the piezoresistive fabric.

24. The sensor system of claim 22, wherein the sensor traces are on both sides of the piezoresistive fabric.

25. The sensor system of claim 24, wherein a first one of the sensor traces on one side of the piezoresistive fabric is electrically connected to a first one of the routing traces on an opposing side of the piezoresistive fabric using a via through which conductive material is flowed, using a metal via, or using a metal rivet.

26. The sensor system of claim 22, further comprising second insulating material formed over a first one of the routing traces, wherein at least a portion of a second one of the routing traces is formed over the second insulating material and the first routing trace.

27. The sensor system of claim 22, wherein at least some of the sensor traces are electrically connected via corresponding ones of the routing traces to corresponding conductors in a connector at an edge of the piezoresistive fabric.

28. The sensor system of claim 27, wherein the connector comprises an elastomeric connector that alternates conductive and non-conductive rubber, a flexible circuit board, conductive threads configured for connection to an external assembly, or a bundle of conductors connected to the piezoresistive fabric with a conductive adhesive and/or rivets, the conductive adhesive and/or rivets making electrical connections to the routing traces.

29. The sensor system of claim 22, wherein a first sensor trace is characterized by a first conductivity and a second conductive sensor trace is characterized by a second conductivity lower than the first conductivity, the sensor system further comprising circuitry configured to drive one end of the second sensor trace with a first signal characterized by a first duty cycle, and to drive an opposing end of the second sensor trace with a second signal characterized by a second duty cycle, the circuitry being further configured to receive a mixed signal from the first sensor trace, the mixed signal including contributions from the first and second signals via the piezoresistive fabric, the circuitry being further configured to detect a location of a touch event along a first axis of the second sensor trace with reference to the contributions of the first and second signals to the mixed signal.

30. The sensor system of claim 29, wherein the sensor traces include a third sensor trace characterized by the second conductivity, wherein the circuitry is further configured to drive one end of the third sensor trace with a third signal characterized by a third duty cycle, and to drive an opposing end of the third sensor trace with a fourth signal characterized by a fourth duty cycle, wherein the mixed signal includes contributions from the third and fourth signals via the piezoresistive fabric, and wherein the circuitry is further configured to detect the location of the touch event along a second axis of the second and third sensor traces with reference to the contributions of the third and fourth signals to the mixed signal.

31. A controller, comprising:

piezoresistive fabric;

a plurality of sensor trace groups printed, screened, or deposited directly on one or more surfaces of the piezoresistive fabric, the plurality of sensor trace groups and the piezoresistive fabric forming a plurality of sensors, each of the sensor trace groups corresponding to a sensor of the plurality of sensors and including two or more sensor traces on a same side of the piezoresistive fabric, wherein resistance between the sensor traces in each of the sensor trace groups varies with force applied to the piezoresistive fabric in a vicinity of the sensor trace group;

first insulating material printed, screened, or deposited directly on one or more of the surfaces of the piezoresistive fabric; and a plurality of routing traces printed, screened, or deposited on the first insulating material and connected to corresponding ones of the sensor trace groups; and circuitry configured to receive one or more signals from each of the trace groups via corresponding ones of the routing traces and generate control information in response thereto, the control information being for controlling operation of one or more processes or devices in communication with the circuitry.

32. An article of clothing including the controller of claim 31.

33. The controller of claim 31, wherein the one or more processes or devices includes a music player, and wherein the sensor trace groups include a volume control, a navigation control, and playback controls for the music player.

34. The controller of claim 33, wherein the one or more processes or devices includes a mobile phone, and wherein the sensor trace groups include a phone call answering and termination control for the mobile phone.

35. The controller of claim 31, wherein the sensor trace groups include an enable/disable control for the controller.

* * * * *